(12) United States Patent
Vanderwal

(10) Patent No.: US 6,752,956 B1
(45) Date of Patent: *Jun. 22, 2004

(54) WASTE TREATMENT CONTROL SYSTEM

(75) Inventor: Richard A. Vanderwal, Kingston (CA)

(73) Assignee: Hydroclave Systems Corporation, Ontario (CA)

(*) Notice: Subject to any disclaimer, the term of this patent is extended or adjusted under 35 U.S.C. 154(b) by 556 days.

This patent is subject to a terminal disclaimer.

(21) Appl. No.: 09/702,067

(22) Filed: Oct. 30, 2000

Related U.S. Application Data

(63) Continuation-in-part of application No. 08/924,614, filed on Sep. 5, 1997, now Pat. No. 6,139,793.

(51) Int. Cl.[7] ............................................. A61L 11/00
(52) U.S. Cl. .......................... 422/3; 422/309; 366/149; 366/307; 341/606
(58) Field of Search .................. 422/1, 3, 307, 422/309; 366/149, 307; 241/606

(56) References Cited

U.S. PATENT DOCUMENTS

| | | | |
|---|---|---|---|
| 4,236,677 A | 12/1980 | Lodige et al. | 241/172 |
| 4,374,491 A | 2/1983 | Stortroen et al. | 100/73 |
| 4,395,132 A | 7/1983 | Wyffels | 366/147 |
| 4,846,054 A | 7/1989 | Mange et al. | 99/495 |
| 4,847,007 A | 7/1989 | Queiser et al. | 252/628 |
| 4,889,431 A | 12/1989 | Liechti | 366/99 |
| 4,974,781 A | 12/1990 | Placzek | 241/17 |
| 5,084,250 A | 1/1992 | Hall | 422/492 |
| 5,119,994 A | 6/1992 | Placzek | 241/17 |
| 5,186,397 A | 2/1993 | Orlando | 241/23 |
| 5,217,688 A | 6/1993 | Von Lersner | 422/26 |
| 5,346,142 A | 9/1994 | Miller et al. | 241/21 |
| 5,389,347 A | 2/1995 | Hall | 422/307 |
| 5,397,535 A | 3/1995 | Kaneko | 422/22 |
| 5,424,033 A | 6/1995 | Roland | 422/26 |
| 5,437,414 A | 8/1995 | Hall | 241/74 |
| 5,582,793 A | 12/1996 | Glazer et al. | 422/26 |
| 5,614,157 A | 3/1997 | Hall | 422/307 |
| 5,635,122 A | 6/1997 | Vezzani | 264/115 |
| 6,139,793 A | * 10/2000 | Vanderwal | 422/1 |

FOREIGN PATENT DOCUMENTS

| | | |
|---|---|---|
| CA | 1316324 | 4/1993 |
| EP | 0081727 A2 | 6/1983 |
| FR | 2240041 | 3/1975 |
| JP | 01115359 | 5/1989 |

* cited by examiner

*Primary Examiner*—Elizabeth McKane
(74) *Attorney, Agent, or Firm*—Hamilton, Brook, Smith & Reynolds, P.C.

(57) ABSTRACT

The invention relates to a control system for processing waste. The system controls pressure and temperature in a treatment vessel to provide a more efficient process. A system for shredding the waste in the vessel is used to improve process efficiency and provides a more compact waste product.

23 Claims, 19 Drawing Sheets

WASTE TREATMENT CONTROL SYSTEM

RELATED APPLICATION(S)

This application is a Continuation-In-Part of U.S. patent application Ser. No. 08/924,614 filed on Sep. 5, 1997 now U.S. Pat. No. 6,139,793, the entire teachings of which are incorporated herein by reference.

BACKGROUND OF THE INVENTION

Studies conducted in hospitals in the United States and Canada indicate that about 1.5 to 7.5 kg of biomedical waste is generated per bed per day (Ontario Ministry of the Environment "Biomedical Waste Incinerators" Incinerator Design and Operating Criteria Vol. II, October, 1986). Biomedical waste includes used syringes, gowns, bedding, containers, bandages, dressings, used disposable gloves, human waste and other liquid and solid waste materials which may be contaminated with, for example, infectious bacteria and viruses.

Incineration is presently a method of treating the biomedical waste. There are, however, concerns about the environmental impact of incineration, especially with respect to airborne emissions from incineration plants. Accordingly, incinerators must now be equipped with sophisticated emission quality control devices. Such devices are expensive, thereby providing a financial obstacle to the upgrading and/or building of incinerators.

Alternatives to incineration include autoclaves, chemical treatment, microwave and microwave technologies. The most common alternative, is sterilization by steam in an autoclave. The process uses hot steam under pressure to kill bacteria, viruses, parasites and heat-resistant spores and is used extensively in a non-waste treatment manner in laboratories to sterilize equipment, media for bacterial growth and pathogenic cultures.

Sterilization of biomedical waste is achieved by exposing all portions of the waste to a temperature and pressure for a time sufficient to kill bacteria, viruses, parasites and heat-resistant spores. However, since biomedical waste is segregated and packaged in leak-proof, color designed plastic bags (red is the designated color in the United States and yellow is the designated colour in Canada) contained in sealed boxes, heat transfer must often be effected through tightly wrapped packages and plastic bags containing the waste material. The sterilization cycle must then be extended to ensure that all portions of the waste material have been subjected to the desired conditions of temperature and pressure for the appropriate length of time. Accordingly, the time required to achieve sterilization depends on the efficiency of heat transfer which in turn depends on the type of material, density of the material, batch volume and how full the autoclave is loaded. Heat transfer is even further inhibited by entrained air inside the package resulting in cold spots which can interfere with sterilization unless the cycle is sufficiently extended to ensure complete sterility.

Another difficulty is the inability to control internal pressure of the sealed bags and boxes. In particular, bags and packages can explode during the process inside the vessel, making unloading very messy despite the elimination of infectious hazards. The degree to which the contents of the autoclave will explode is somewhat dependent on the length of the cooling cycle after the desired sterilization cycle. This cooling cycle can extend the time in the autoclave by 100% or more.

Sterilization in an autoclave relies on injection of steam directly into the autoclave. Injected steam condenses on the walls of the autoclave and on the outer surfaces of the waste and containers thereof or is absorbed by the waste. The steam condensate is then drained from the autoclave for subsequent disposal. It will be appreciated by those skilled in the art that the steam condensate is generally unsuitable for reuse and represents a significant energy loss as the hot water is drained. Furthermore, the moisture absorbed by the waste can substantially increase the weight of the packages, for example, by about 50%. Accordingly, the moist packages are heavier, more difficult to handle and make unloading cumbersome. Moreover, since dumping costs at landfill sites are typically set on a per ton basis, the increased weight due to moisture retention represents substantial increases in dumping costs.

An alternative to conventional autoclaves is a process for the disposal of medical waste in a pressure vessel fitted with high-speed blades. The blades are provided at the base of the vessel and operate at high rotational speeds (900–3500 rpm). An internal mixer is provided on the lid to direct the waste towards the blades. Steam is injected directly into the vessel for heat transfer. At the end of the sterilization process, the vessel is vented to vacuum to flash off moisture.

Another alternative to the conventional autoclave, is a cylindrical pressure vessel with an elongated cylindrical drum located in the pressure vessel for receiving the waste to be treated. The pressure vessel and the drum are set at an angle, such that the end where the drum is open and the door of the pressure vessel is located is elevated relative to the other end. The drum has a series of lifting paddles on the wall for agitation of the waste material in the drum as the drum is rotated within the pressure vessel. In addition, the drum has a helical flight which work in a counter-current manner with the lifting paddles to mix the waste and when the drum is rotated in the other direction moves the waste out of the drum for removal through the door of the pressure vessel. Water is added to the waste to attempt to receive a content of 75% moisture in the waste. Steam is injected directly into the pressure vessel for heat transfer.

SUMMARY OF THE INVENTION

A preferred embodiment of the invention relates to a control system for a waste treatment processing apparatus. The control system provides a computer automated system that controls operation of the process including the values, monitors pressure and/or temperature, speed and other parameters to increase capacity and improve operating efficiency. The system also records data relating to each processing cycle.

The invention further includes a cutting system to shred the contents during operation. This improves heat transfer to the waste, produces a more compact product and is better suited for recycling of waste product.

In the preferred embodiment the waste does not need to be pre-treated prior to being placed in the pressure vessel. Moisture in the form of water or steam does not need to be added to the pressure vessel for it to work efficiently in most waste composition make-ups. The waste is dried after sterilization to reduce both volume and the weight of the treated waste, therein making it more cost effective for disposal.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Figure 1:
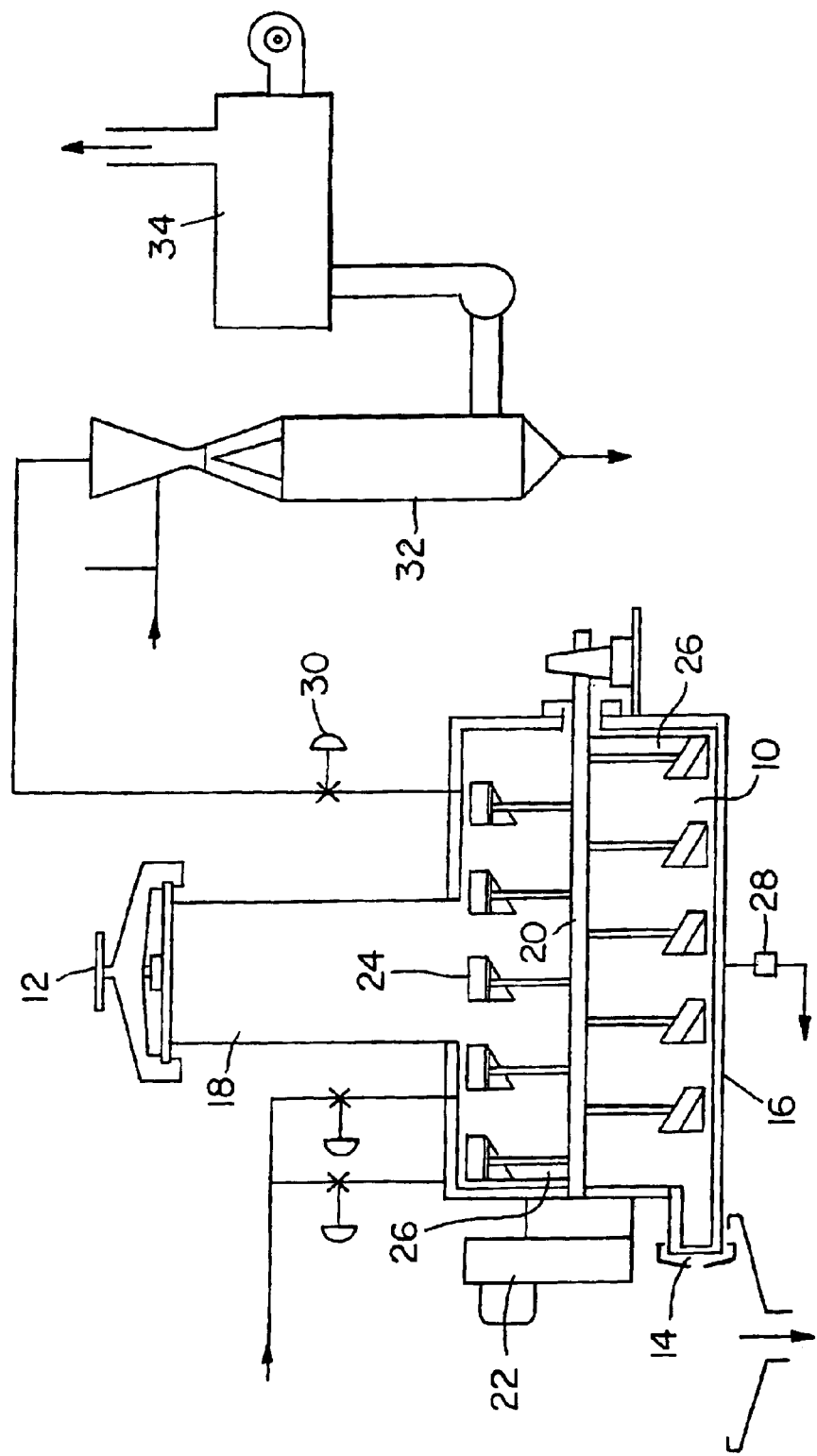
FIG. 1 is a schematic drawing of a process of the present invention.

Referring now to FIG. 1, a pressure vessel 10 is a horizontally disposed cylindrical vessel with an inlet port 12 and an outlet port 14. The pressure vessel 10 is sometimes referred to as a hydrolysis vessel since biological waste, such as tissue, is broken down in the vessel, however the element of water need not be added to the vessel as explained below.

The pressure vessel 10 is jacketed with a steam jacket 16. The inlet and outlet ports 12, 14 are capable of being hermetically sealed. In the embodiment depicted in FIG. 1, the inlet port 12 is provided with a pressure vessel lid. It will be appreciated by those skilled in the art that other means for obtaining a hermetic seal, for example a knife-gate closure, may be used without departing from the scope of the present invention. In the embodiment shown in FIGS. 1 and 2, the inlet port 12 is positioned at the top of the pressure vessel 10, thereby facilitating loading by means of a conveyor belt. Preferably, the inlet port 12 is provided with an extended neck 18 to prevent liquids from splashing out of the pressure vessel 10 during the loading step. Advantageously, a substantially downward flow of air is induced in the inlet port 12 to prevent the escape of any airborne emissions during loading. The downward flow of air may be induced, for example, by applying a negative pressure in the inlet port 12.

The pressure vessel 10 is provided with a shaft 20 which extends axially along the full length of the vessel 10. The shaft 20 is powered by a drive mechanism 22.

The shaft 20 is also provided with mixing paddles 24 to tumble the waste against the heated walls of the pressure vessel 10 thereby facilitating uniform heating of the waste. In the embodiment shown in FIG. 1, the mixing paddles 24 are depicted as directional scoop blades. The directional scoop blades serve to mechanically break the waste into smaller components and to tumble the waste against the walls of the pressure vessel 10 when rotated in one direction and to direct the waste towards the outlet port 14 during an unloading step when rotated in the opposite direction. Rotation of the mixing paddles 24 during loading of the pressure vessel 10 allows the vessel 10 to be tightly loaded with waste. The mixing paddles 24 may be provided with a mechanism to adjust the tolerance between the mixing paddles 24 and the wall of the pressure vessel 10. As shown in FIG. 1, the mixing paddles 24 at both ends of the pressure vessel 10 may also be provided with a scraper 26 to facilitate removal of the waste during the unloading step. In the embodiment shown in FIG. 1, the mixing paddles 24 are arranged about the shaft 20 at an angle of 180 relative to one another. However, the mixing paddles 24 may be arranged at angles of 120 or 90 relative to each other, such that efficient mixing of the waste is provided during sterilization. Two or more mixing paddles 24 may extend from the same point on the shaft 20 or may be spaced radially along the shaft 20 as shown in FIG. 1.

The pressure vessel 10 is heated by pressurizing the steam jacket 16 with steam. The steam is not in direct contact with the waste being treated and any steam which condenses inside the steam jacket 16 is drained via a trap 28 for reheating in a boiler before being returned to the steam jacket 16. This is particularly advantageous as compared to a conventional autoclave wherein steam condensate represents an energy loss of approximately 18%. Furthermore, the steam condensate increases the moisture content of the waste which corresponds to increased weight and problems with handling after the sterilization cycle. In accordance with the present invention, the steam does not directly contact the waste so that substantially all of the condensate may be recovered and recycled. Moreover, the waste does not pick up any excess moisture.

The heating cycle may be further enhanced by providing heat to the interior of the shaft 20. This may be accomplished by providing a steam line through the drive mechanism 22 to the interior of a hollow shaft 20. The condensate may be directed to the condensate line connected to the trap 28.

In operation, biomedical and/or other hazardous waste material is loaded into the pressure vessel 10 through the inlet port 12. Preferably, the mixing paddles 24 of the shaft 20 are rotated by activating the drive mechanism 22 to enable the pressure vessel 10 to be loaded to a greater capacity. The shaft 20 is preferably rotated at a low rotational speed, for example at about 5 rpm, to reduce splashing of liquids through the inlet port 12 while the waste is being loaded. A downward flow of air is advantageously induced in the inlet port 12 to prevent the escape of airborne emissions through the inlet port 12 during loading. The plastic bags and boxes in which the waste is stored are broken by the action of the rotating mixing paddles 24 and the waste is broken into smaller components.

The inlet port 12 is then hermetically sealed and the integrity of the seal between the pressure vessel 10 and the inlet and outlet ports 12, 14, respectively, is confirmed by conventional electrical interlocks.

Steam is fed into the steam jacket 16 while the shaft 20 and the mixing paddles 24 are rotated. The shaft 20 is suitably rotated at a speed of from about 5 to 50 rpm so that successive portions of the waste material contact the walls of the pressure vessel 10 whereby the contents of the vessel 10 are heated substantially uniformly. The heating cycle may be further enhanced by the provision of steam to the interior of the shaft 20.

When the interior of the pressure vessel 10 and the waste material contained therein reaches a temperature of 100° C. (212 F.), moisture in the waste material is converted to steam, thereby increasing the pressure within the pressure vessel 10. Heating is continued until a pressure in the range of from about 15 to 100 psig, corresponding to a temperature in the range of from about 121° to 170° C. (250 to 338 F.), is achieved. Preferably, the pressure inside the pressure vessel 10 is regulated so that the temperature is not so high that plastic wastes chemically degrade.

The combined action of the mixing paddles 24 and the heat supplied by the steam jacket 16 cause the waste inside the pressure vessel 10 to further break down into smaller pieces. As bags and other containers are broken, any entrained air is released inside the pressure vessel 10. Accordingly, cold spots are substantially eliminated. Furthermore, the effects of the type of material, density of the material, batch volume and the degree to which the vessel is loaded are substantially reduced in the pressure vessel 10 and process of the present invention, especially as compared to a conventional autoclave.

Circulation of the smaller portions of waste material within the pressure vessel 10 allows for a more even heat distribution and a reduction of temperature gradients throughout the waste contained therein, ensuring that all portions of the waste material are exposed to the appropriate temperature and pressure for a period of time sufficient to achieve sterilization of the material. It will be appreciated by those skilled in the art that the time required to achieve sterilization is substantially reduced as compared to the time required in a conventional autoclave wherein the heat must penetrate the relatively large pieces of waste material, especially waste contained in plastic bags and other containers.

There is generally sufficient moisture in biomedical waste to pressurize the pressure vessel 10 to the desired operating pressure and temperature. However, if the moisture content of the waste material is unusually low, for example less than 10%, there may be insufficient moisture to pressurize the pressure vessel 10. A situation wherein the moisture content is insufficient can be detected by monitoring pressure and temperature gauges. If there is insufficient moisture, the pressure inside the pressure vessel 10 does not increase with an increase in temperature and the desired combination of temperature and pressure to effect sterilization may not be realized. This may be overcome by injecting high pressure steam, which may be tapped off the jacket supply steam line at 40 to 150 psig, directly into the pressure vessel 10 to increase the moisture content therein. In this way, the moisture content inside the pressure vessel 10 is not unduly increased. Alternatively, water may be added to the pressure vessel 10 during the loading step. However, this method is not as efficient and not as easy to monitor.

A thermocouple and temperature controller can be used in a preferred embodiment, however, in certain embodiments it is not necessary to monitor or control the temperature of the waste contained in the pressure vessel 10, since pressure regulation will achieve the desired temperature control and reference may be made to standard steam tables to automatically determine the temperature which corresponds to an actual measured pressure, if desired. A low moisture condition can be sensed by monitoring pressure increases and the rate thereof. An operator can thus determine, after a period of heating, whether there is a sufficient increase in pressure to indicate sufficient moisture.

After the desired treatment time, the pressure vessel 10 is de-pressurized to atmospheric pressure. Preferably, the pressure vessel 10 is vented through a vent 30 at a controlled rate to a condenser 32. The condenser 32 cools the gases from the pressure vessel 10, for example, to a temperature of about 140 F., thereby condensing the moisture in the gas into the water contained in the condenser 32. Any particulates present in the gas will be removed in the condenser 32.

In the case where the waste material contains polyvinyl chloride, the gases from the pressure vessel 10 and, therefore, the condenser 32, may contain hydrochloric acid. Accordingly, the water in the condenser 32 is preferably neutralized with a caustic feed prior to being drained to a sanitary sewer.

The cooled gases from the condenser 32 are nontoxic but may have an odor. Accordingly, the cooled gases are preferably subsequently passed through an air scrubber 34 for the appropriate heat, chemical and/or mechanical treatment which may dictated by local regulatory authorities. For example, with respect to heat treatment of gases, authorities in Ontario regulate that the gases be treated at 1800 F. with a residence time of 0.75 second before being discharged to the environment.

Preferably, the pressure vessel 10 is depressurized while heating is continued by maintaining steam input to the steam jacket 16. In this way, substantially all of the moisture in the waste material will evaporate. While the volume of the waste is reduced during the entire process of the present invention, the reduced water content and mechanical agitation act during the de-pressurization step act to further reduce the volume of the treated waste. Depending on the moisture content, density and other characteristics of the waste, it is possible to reduce the volume to about one-fifth of the original volume of waste material. The reduced moisture content represents a decrease in the weight of the treated waste in addition to reduced landfill and transportation costs.

The outlet port 14 is then opened and the shaft 20 and mixing paddles 24 are rotated in a direction to cause the treated waste to move toward the outlet port 14. The scrapers 21 assist in removing the waste from the end walls of the pressure vessel 10. The hydrolysed waste material is thus emitted from the vessel 10.

The entire process can, of course, be accurately controlled in terms of time, temperature, pressure and flow. For example, during de-pressurization of the pressure vessel 10, the gas flow can be controlled, or shut off, if the operating parameters of the condenser 32 and the air scrubber 34 deviate from normal values to an unsafe level. Similarly, the operating time, temperature and pressure of the pressure vessel 10 can be interlocked with the vent 30 to prevent gases from escaping prior to sufficient sterilization of the waste. These indicators can be recorded on a strip or circular graph, as is commonly used in conventional autoclaves. The control system could also be adapted to include information on waste classification and waste origin on the graph.

In accordance with the present invention, it is possible to provide economic and effective waste treatment at individual medical treatment facilities. It may be feasible to utilize existing steam plants at these medical treatment facilities as an energy source. Furthermore, the cost and potential hazards associated with the transport of biomedical waste would be eliminated.

While it is preferable to avoid transport of untreated biomedical waste, a central waste treatment facility based on the process of the present invention could be used to serve a number of medical treatment facilities. The latter waste treatment facility may be constructed as illustrated in FIG. 2.

In the case where biomedical and/or other hazardous waste must be transported to a central waste treatment facility, the waste is preferably transported in a refrigerated truck 38 to a collection area 40. The waste material is conveyed to a treatment area 42, for example, via a belt conveyor 44. The waste material is then loaded into the pressure vessel 10 in the treatment area 42. After the waste has been sufficiently sterilized, the pressure vessel 10 is de-pressurized by venting the gases to the condenser 32. The cooled gases which have not condensed in the condenser 32 are treated in the air scrubber 34 and vented to the atmosphere through an air scrubber stack 46. The de-watered waste material is unloaded from the pressure vessel 10 and conveyed to a loading area 48, for example, via a screw conveyor 50. The treated waste is then transported to a landfill site by a truck 52.

Figure 2:
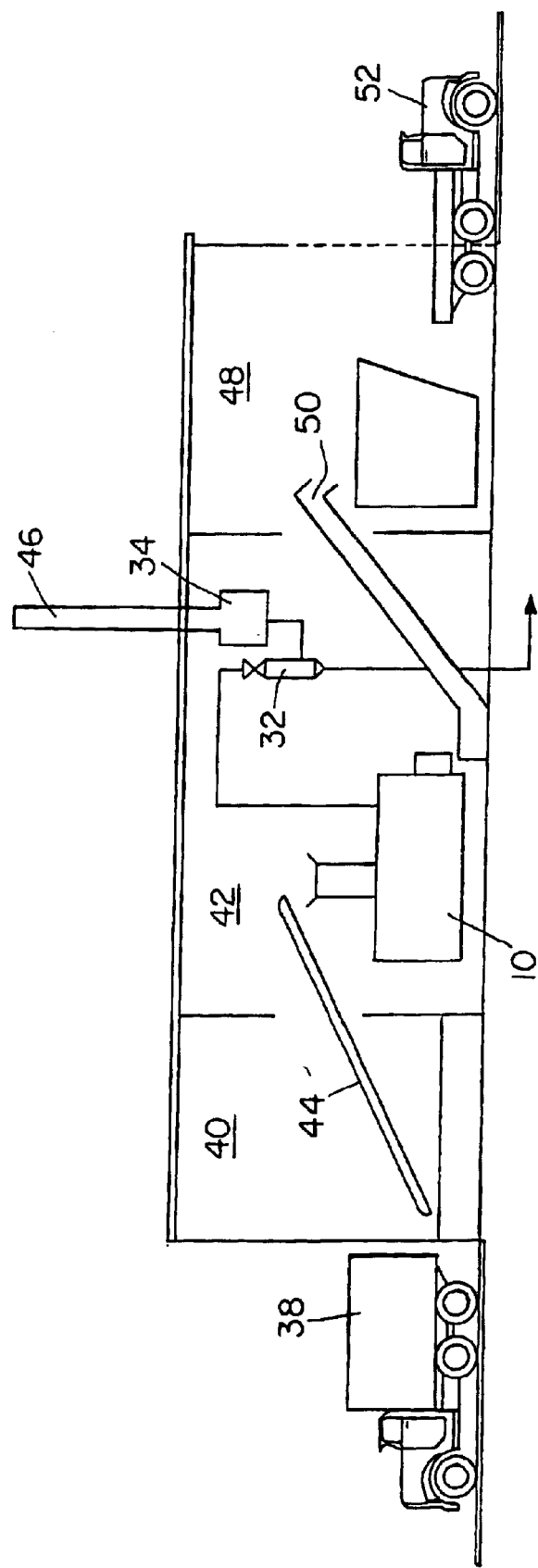
FIG. 2 is a schematic drawing of a material flow in a treatment facility equipped to carry out the process of the present invention.

The treatment facility illustrated in FIG. 2 is significantly less expensive to construct and operate than an incinerator facility of equal capacity.

A waste treatment plant, constructed as illustrated in FIG. 2, can include one or two boiler stacks and a small fume incinerator stack protruding above the roof. Furthermore, the plant does not emit any discernible odors or display large visible plumes of smoke from the stacks.

Figure 3:
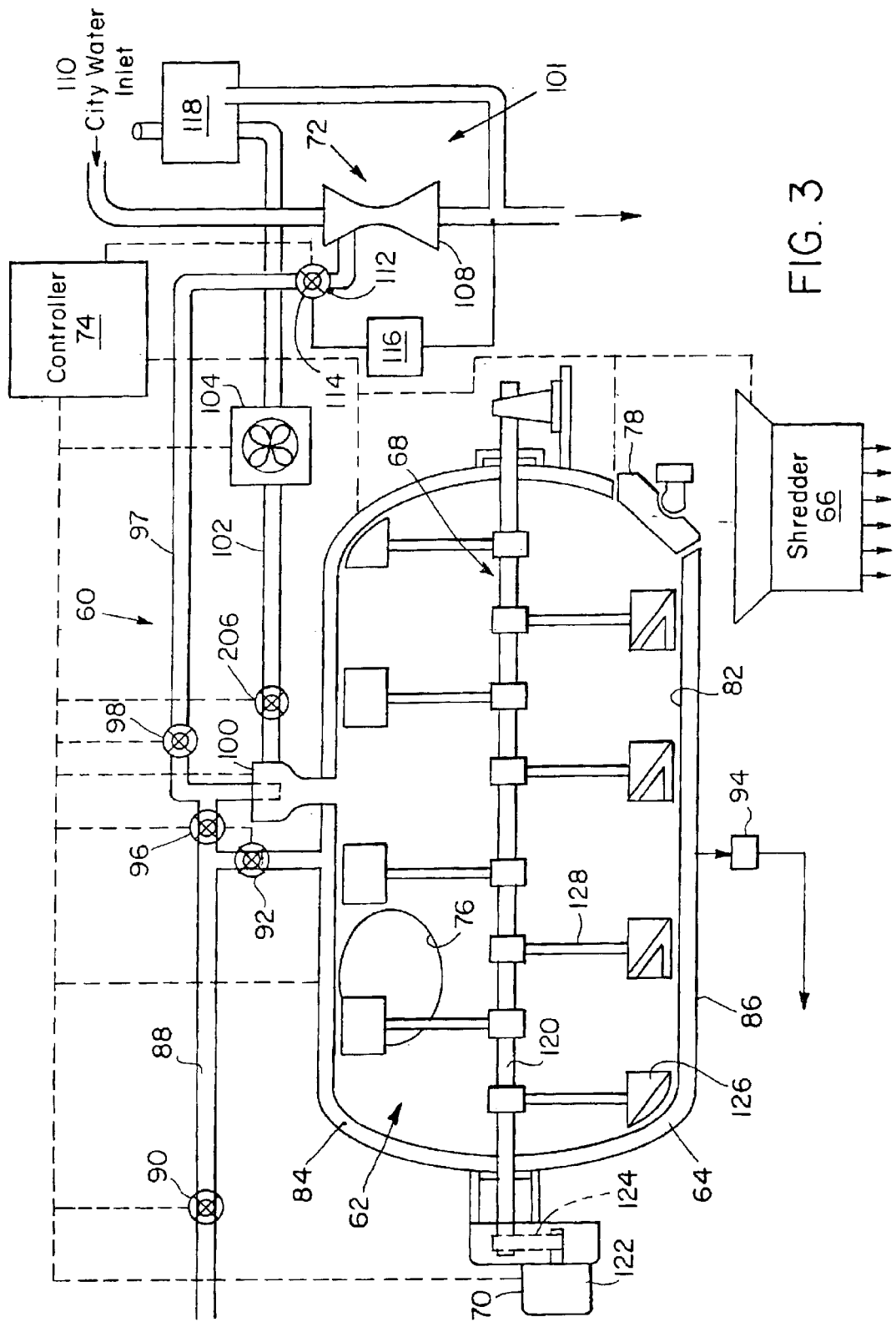
FIG. 3 is a schematic of a processing apparatus according to the invention.

A schematic of an alternative embodiment of a processing apparatus 60 is shown in FIG. 3. The processing apparatus 60 has a pressure vessel 62, a heating jacket 64 substantially surrounding the pressure vessel 62, a shredder 66, an agitating mechanism 68 with a driver 70, a vapor condensing system 72 and a controller 74. The pressure vessel 62 has an inlet port, a loading door 76, and an outlet port, an unloading door 78. The loading door 76 is for receiving the untreated waste. The waste does not require any pre-processing treatment.

The pressure vessel 62 is substantially a cylindrical tube with a domed end. The pressure vessel 62 is surrounded by the heating jacket 64 which is capable of transferring heat to the exterior walls 82 of the pressure vessel 62. One embodiment of the heating jacket 64 is a space 84 defined by the exterior walls 82 of the pressure vessel 62 and an outer exterior wall 86; this double walled vessel is capable of containing a heated liquid or gas. An alternative embodiment of the heating jacket 64 is heated elements embedded in a material, such as heating wires in an electrically insulative but thermally conductive material. The heating jacket 64 is covered with an insulating material such that the heat is directed towards the pressure vessel and not to the surrounding environment, such as a waste treatment room.

In a preferred embodiment, the heating jacket 64 is a steam jacket. The steam flows from a boiler in a steam line 88 through a first steam valve 90 and a second steam valve 92, which can operate manually and be connected to the controller 74 to operate automatically, into the space, volume, 84 of the steam jacket 64. The steam in the steam jacket 64 is not in direct contact with the waste being treated in the pressure vessel 62. Any steam which condenses inside the steam jacket 64 is drained via a steam trap 94 for reheating in the boiler before being returned to the steam jacket 64. This is particularly advantageous as compared to a conventional autoclave wherein steam condensate represents an energy loss of approximately 18%.

The steam line 88 is in addition connected to the pressure vessel 62 via a third steam valve 96 to allow the addition of steam to the pressure vessel 62 if needed, as described below. The pressure vessel 62 is also connected to the vapor condensing system 72 through a vapor exhaust line 97 and a fourth steam valve 98. The steam valves 90, 92, 96, and 98 are controlled by the controller 74 as explained below.

It is recognized that the third steam valve 96 and the fourth steam valve 98 could be combined into one three-way valve having the positions of off; steam from the boiler to the pressure vessel; and steam/vapor from the pressure vessel to the vapor condensing system. Steam from the boiler is not fed directly to the vapor condensing system.

The steam line 88 is connected to the pressure vessel 62, in addition to through the third steam valve 96, through a venting/filter system 100 attached to the pressure vessel. The venting/filter system 100 limits what particles leave the pressure vessel towards the vapor condensing system 72. The venting/filter system 100 will be described in detail below in reference to FIG. 10.

In addition to the vapor exhaust line 97 that carries vapor from the pressure vessel 62 to the vapor condensing system 72 of the vented emission treatment system 101, a second line extends from the venting/filter system 100 to a gas portion 118 of the vented emission treatment system 101. The line is part of a negative air pressure device 102 and has a fan 104 for creating a low pressure to draw air into the pressure vessel 62 through the loading door when loading to prevent the escape of any airborne emission during loading during filing.

The vapor condensing system 72 receives the steam, moisture or gas that is drawn away or forced away from the pressure vessel through the venting/filter system 100, as described below. The vapor condensing system 72 has a cooling system 108, which, in a preferred embodiment, is connected to a water system 110 such a city potable system, a fire drain pipe system, or other water source including gray water. The steam, moisture or gas which leaves the pressure vessel 62 is cooled and turned back into a liquid by the vapor condensing system 72 by the water from the water system 110 flashing the steam into liquid in the cooling system 108 prior to placing the steam, which is now a liquid, into a sewer system. The vapor condensing system 72 has a temperature sensor 112 which monitors the temperature of the water leaving the cooling system 108 and entering the sewer system. The temperature sensor 112 is connected to a valve 114 in the line from the pressure vessel through a controller 116. The valve 114 limits the flow of steam into the cooling system 108 so that the water from the water system 110 is capable of keeping the temperature of the liquid entering the sewer system below 65.5° C. (150° F.), as explained below. The controller 116 for monitoring the temperature can be a portion of the controller 74.

Those gases in the vapor condensing system 72 which are not condensible are vented through the gas portion 118 of the vented emission treatment system 101. The gas portion 118 is connected to the cooling system 108 through a vent pipe 120, similar in concept to a vent stack in a normal sewer system. The gas portion 118 has an active charcoal filter or a HEPA filter at the top of the stack through which the gases pass in order to remove odor. All the steam, moisture or gas has been retained in the pressure vessel for the designated temperature and time period and therefore can be treated prior to discharging and can be treated as normal waste.

Figure 4:
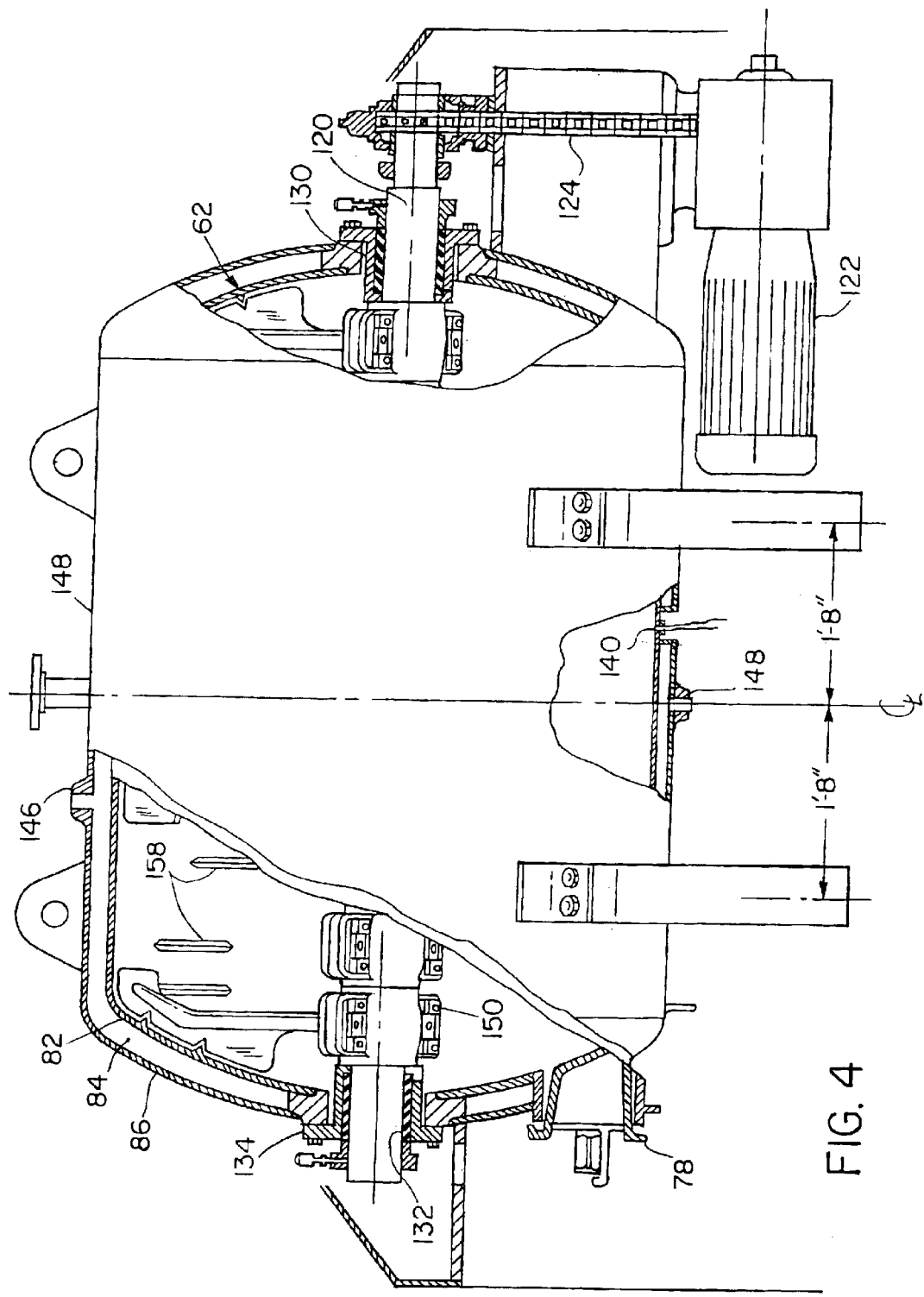
FIG. 4 is a side view of a pressure vessel according to the invention with portions shown in section.

The agitating mechanism 68 has a shaft 120 which extends longitudinally through the pressure vessel 62 and is connected to the driver 70. The driver 70 in a preferred embodiment has an electric motor 122 which rotates the shaft 120 via a transmission mechanism 124, such as a gear box, a chain, or a belt, as best seen in FIG. 4. The agitating mechanism 68 has a plurality of paddles 126 which are located in proximity to the walls 82 of the pressure vessel 62 and spaced from the shaft 120 each by an arm 128. The paddles are directional scoop blades which serve to mechanically break the waste into smaller components and to tumble the waste against the walls 82 of the pressure vessel 62 when rotated in one direction, thereby facilitating uniform heating of the waste. The paddles 126 direct the waste towards the outlet port, unloading door, 78 when rotated in the opposite direction. Rotation of the mixing paddles 126 during loading of the pressure vessel 62 allows the pressure vessel 62 to be tightly loaded with waste.

The shredder 66 is located in proximity to the unloading door 78 of the pressure vessel 62. The shredder 66 takes the waste which has been treated in the pressure vessel 62, as explained below, and further breaks up and shreds the waste into smaller pieces. The shredder 66 is not required to process the biomedical waste to result in sterile waste. The shredder 66 is desired to take the treated waste and further shred it so that the waste no longer has the look of medical waste and makes apparent to medical waste handlers that the waste has been treated.

The entire processing apparatus is controlled by the controller 74. The controller 74 takes inputs from monitors and sensors, and the controller 74 administers the process and records data. The controller 74 will be explained in greater detail below.

Figure 6:
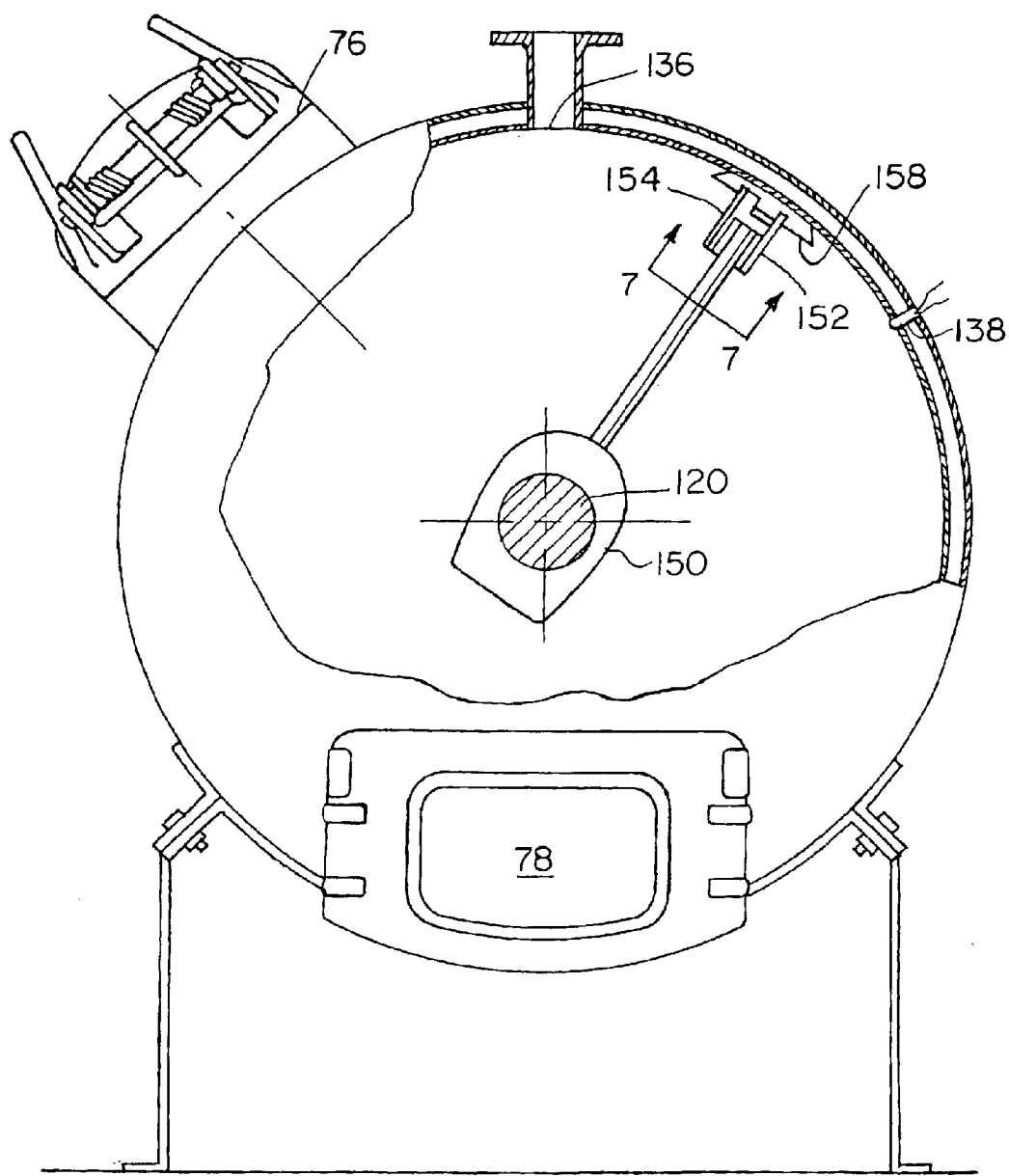
FIG. 6 is an end view of the pressure vessel with a portion broken away showing the interior including paddles.

Referring to FIG. 4, the pressure vessel 62 is substantially a cylindrical shell with domed ends to create the closed vessel. While the operating pressure is not considered extremely high pressure, it is desired in the preferred embodiment to minimize the openings in the pressure vessel 62. In a preferred embodiment, the pressure vessel is made from 1 inch thick steel. In addition to the inlet port 76, seen in FIGS. 3 and 6, and the outlet port 78, the pressure vessel has a pair of openings 130 for receiving the shaft 120 of the agitating mechanism 68. Each end of the shaft 120 extends through a seal 132 in the opening 130. The seal 132 prevents the seepage of waste out of the pressure vessel 62, as explained below. The shaft 120 is supported at each end by a bearing 134, located outside of the pressure vessel 62. The pressure vessel 62 also has a hole 136, as seen in FIG. 6, to which the venting/filter system 100 is connected. In a preferred embodiment, the hole has a 4 inch diameter. The pressure vessel 62 in addition has two openings for monitors or sensors.

Figure 5:
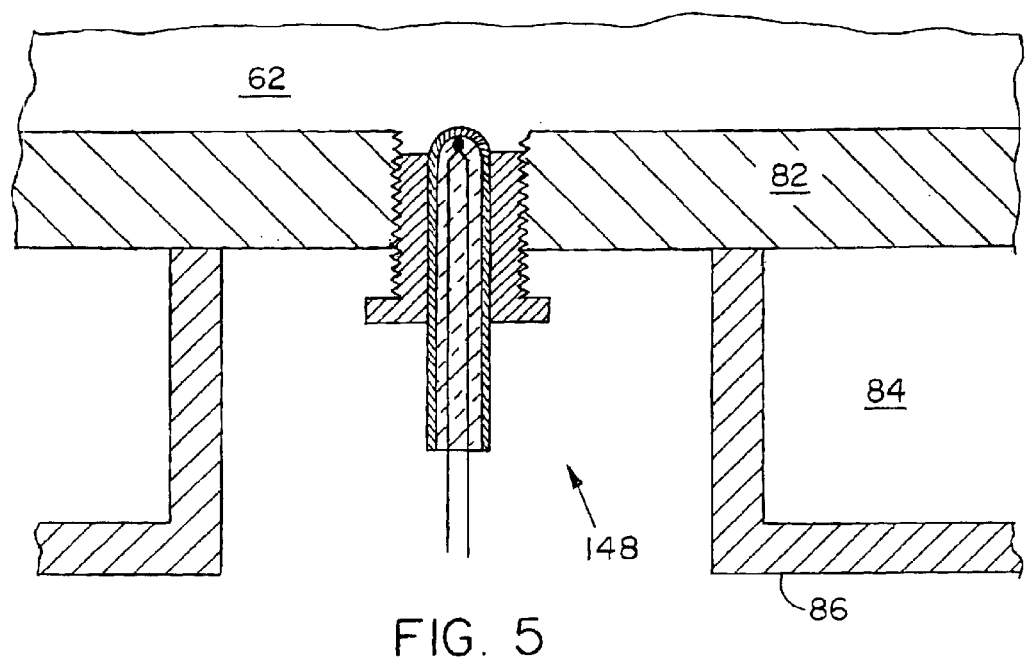
FIG. 5 is an enlarged view of the temperature sensor.

A pressure sensor 138, as seen in FIG. 6, monitors the pressures and in a preferred embodiment is located in the upper portion of the pressure vessel 62. A temperature sensor 140 measures the temperature within the pressure vessel 62. In a preferred embodiment, the temperature sensor 140 is located in the lowest portion of the pressure vessel 62. While the pressure of the pressure vessel 62 is generally uniform throughout, the temperature is more likely to vary in the pressure vessel 62, at least initially. The temperature is the lowest generally at the bottom initially as explained below. The temperature sensor 140, a thermocouple, has an iron-constantan tip. The temperature sensor, such as the one described above, is sold by Honeywell. The outer wall 86 of the heating jacket 64 is formed such that there is an opening around the temperature sensor 140. An insulating plug or ring 142 is located between the temperature sensor 140 and the wall 82 of the pressure vessel 62 as seen in FIG. 5 so that the outer wall 82 of the pressure vessel 62 and the heating jacket 64 do not influence the reading of the temperature sensor 140. Both the temperature sensor 140 and the pressure sensor 138 are connected to the controller 74 shown in FIG. 3.

Still referring to FIG. 4, the heating jacket 64 in a preferred embodiment is a steam jacket and is defined by the wall 82 of the pressure vessel 62 and the outer exterior wall 86. In a preferred embodiment the outer exterior wall 86 is $3/8$ to $1/2$ inch thick steel and has a 2 inch thick insulating layer of glass fiber or mineral wool on the outside and an outer layer of stainless steel covering the insulating layer. In addition to opening to allow access to openings in the wall 82 of the pressure vessel, the outer exterior wall 86 has three additional openings: an opening 144 for allowing steam from the steam line 88 into the space 84 in the steam jacket 64, an opening 146 to the steam trap 94, as seen in FIG. 3, for the collection of condensed steam; and an opening 148 for the removal of trapped air in the steam jacket 64.

The inlet port, a loading door, 76 of the pressure vessel 62 is located 45° from the top on one side in a preferred embodiment, as shown in FIG. 6, for facilities where the waste is placed in the processing apparatus 60 from within the same waste treatment area, in contrast to from a room above as in the first embodiment. The loading door 76 is located generally at the opposite end of the pressure vessel 62 from the outlet port, an unloading door 76, as best seen in FIG. 3. The unloading door 78 is located at one end of the pressure vessel 62 at the lowest level of the pressure vessel 62 so that the agitating mechanism 68 can push the waste out after treating. The loading door 76 is for receiving the untreated waste. The waste does not require any preprocessing treatment prior to being placed through the loading door 76 into the pressure vessel 62.

Referring to FIGS. 4 and 6, the shaft 120 of the agitating mechanism 68 extends longitudinally through the pressure vessel 62 and is connected to the driver 70, the electric motor 122 in preferred embodiment via a gear drive 124. Located at the other end of the pressure vessel from the electric motor 122 is a bearing 134, a pillow block bearing, for rotatably receiving the other end of the shaft 120. The plurality of paddles 126 are mounted to the shaft 120 by the arm or rod 128 extending from a clamp 150 bolted to the shaft 120 to the paddle 126. Each paddle 126 has a pair of blades 152 and 154. The blades 152 and 154 are joined at one edge 156. One blade 152 is parallel to the shaft 120 and generally moves the waste in a series of planes perpendicular to the shaft 120 as the shaft 120 rotates in one direction, for example clockwise as shown in FIG. 6. The other blade 154 is angled relative to the shaft 120 such that the face of the blade opens towards the end of the pressure vessel 62 that has the unloading door 78. Therefore when the shaft 120 is rotated in the opposite direction, for example counter-clockwise in FIG. 6, the waste is moved towards the unloading door 78.

The pressure vessel 62 has a series of knife edges 158 that interact with the blades 152 and 154 of the paddles 126 to reduce or eliminate tangling of waste on the paddles 126. The knife edges 156 are located on the walls 82 of the pressure vessel 62, and on the upper half of the pressure vessel 62 in a preferred embodiment.

Figure 7:
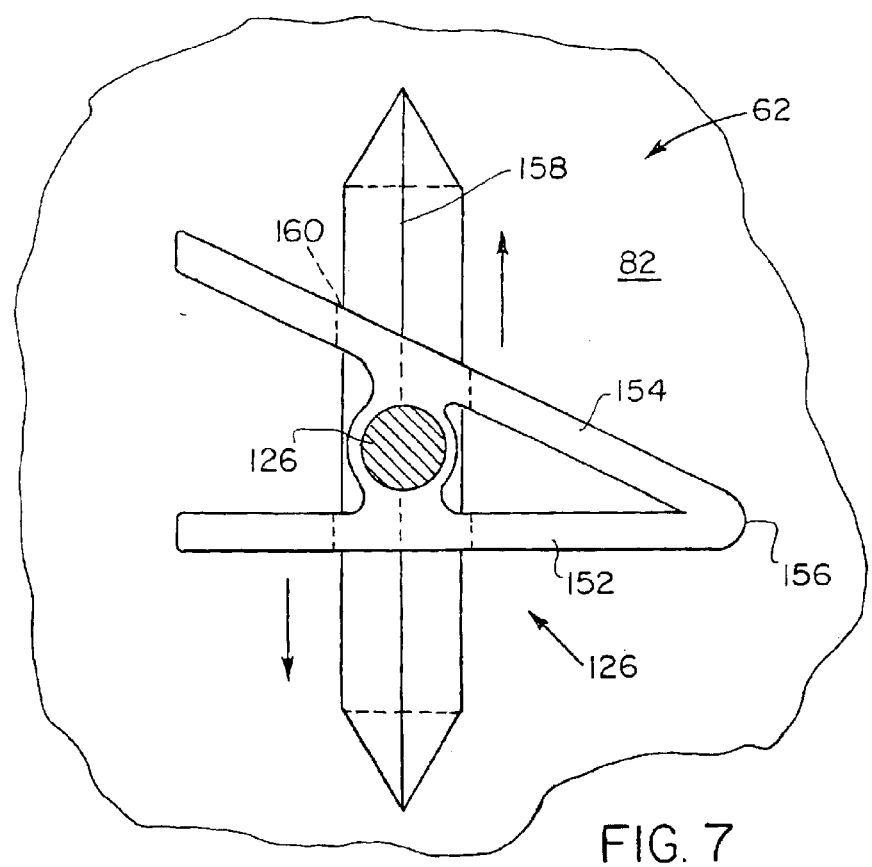
FIG. 7 is an enlarged view of a paddle interacting with the wall of the pressure vessel taken along line 7—7 of FIG. 6.
Figure 8:
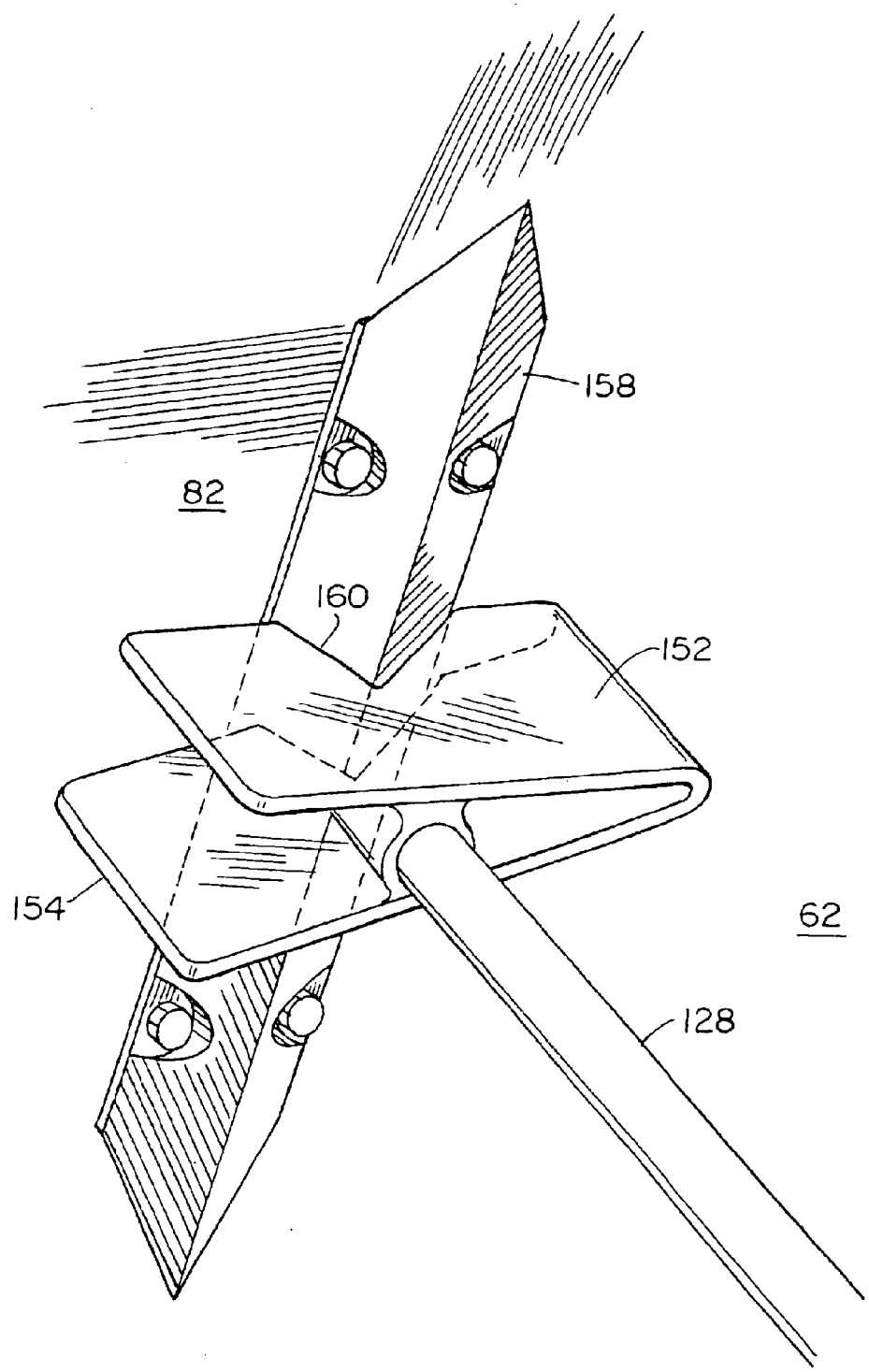
FIG. 8 is a perspective view of a paddle interacting with the wall of the pressure vessel.

An enlarged view of the interaction of the blades 152 and 154 of a paddle 126 and the knife edge 158 mounted on the wall 82 of the pressure vessel 62 is shown in FIGS. 7 and 8. FIG. 7 is a sectional view through the arm or rod 128 of the paddle 126. The blade 152 which is parallel to the shaft 120 is shown below and the blade 154 which is angled is shown on the top, therefore if the paddle 126 is rotating downward in this FIG. the waste would be rotated in planes parallel to the shaft 120 and if the paddle is rotating upward as seen in this FIG., the waste would be moved to the right, towards the end of the pressure vessel 62 that has the unloading door 78.

The blades 152 and 154 each have a slot 160, shown in hidden line, which is aligned with the knife edge 158 mounted on the wall 82 of the pressure vessel 62. The paddle 126 as it rotates may pick up waste which gets tied up or wound around the paddle 126 and does not drop back into the accumulation of waste located in the lower portion of the pressure vessel 62 as the paddle 126, or at least the blades 152 and 154, rises above the top of the accumulation of waste in the pressure vessel 62. Typically waste that would get wound around the paddle 126 includes cloth bandages, sheets, large plastic bags, rubber hoses and other fibrous material or plastic material items that are flexible and are large enough to wrap around. The knife edges 158 cut or tear those items that are caught on the blades 152 and 154 of the paddle 126 and are brought into engagement with the knife edge 158. In a preferred embodiment, the knife edges 158 are located on the upper portion of the pressure vessel 62, so that the likelihood of damage to the knife edges 158 by large heavy objects, such as metal bars and toilet seats is minimized. It is recognized that even when treating medical waste, the processing apparatus 60 will receive items that are not considered medical waste, but nonetheless must be handled by the apparatus 60.

A perspective view of the knife edge 158 as the slot 160 in the blades 152 and 154 of the paddle 126 pass over is shown in FIG. 8. The knife edge 158 is triangular in cross section and trapezoid shape with the largest edge spaced from the wall 82 of the pressure vessel 62. The ends are triangular in shape with the apex of each end projected outward from the base and spaced from the wall 82 of the pressure vessel 62. The knife edge 158 is secured to the wall 82 of the pressure vessel 62 by a series of bolts in a preferred embodiment. If a knife edge 158 is damaged, it can be replaced by unbolting the damaged knife edge 158 and installing a new knife edge. The paddles 126 which are adjacent to the domed ends, especially the end having the unloading door 78, are preferred to have a series of knife edges 158 as best seen in FIG. 4. While the knife edge 158 is shown as a solid bar in FIGS. 7 and 8, it is recognized that the knife edge 158 could take other forms including a right angle bar with the long edges engaging the wall of the pressure vessel.

Figure 9:
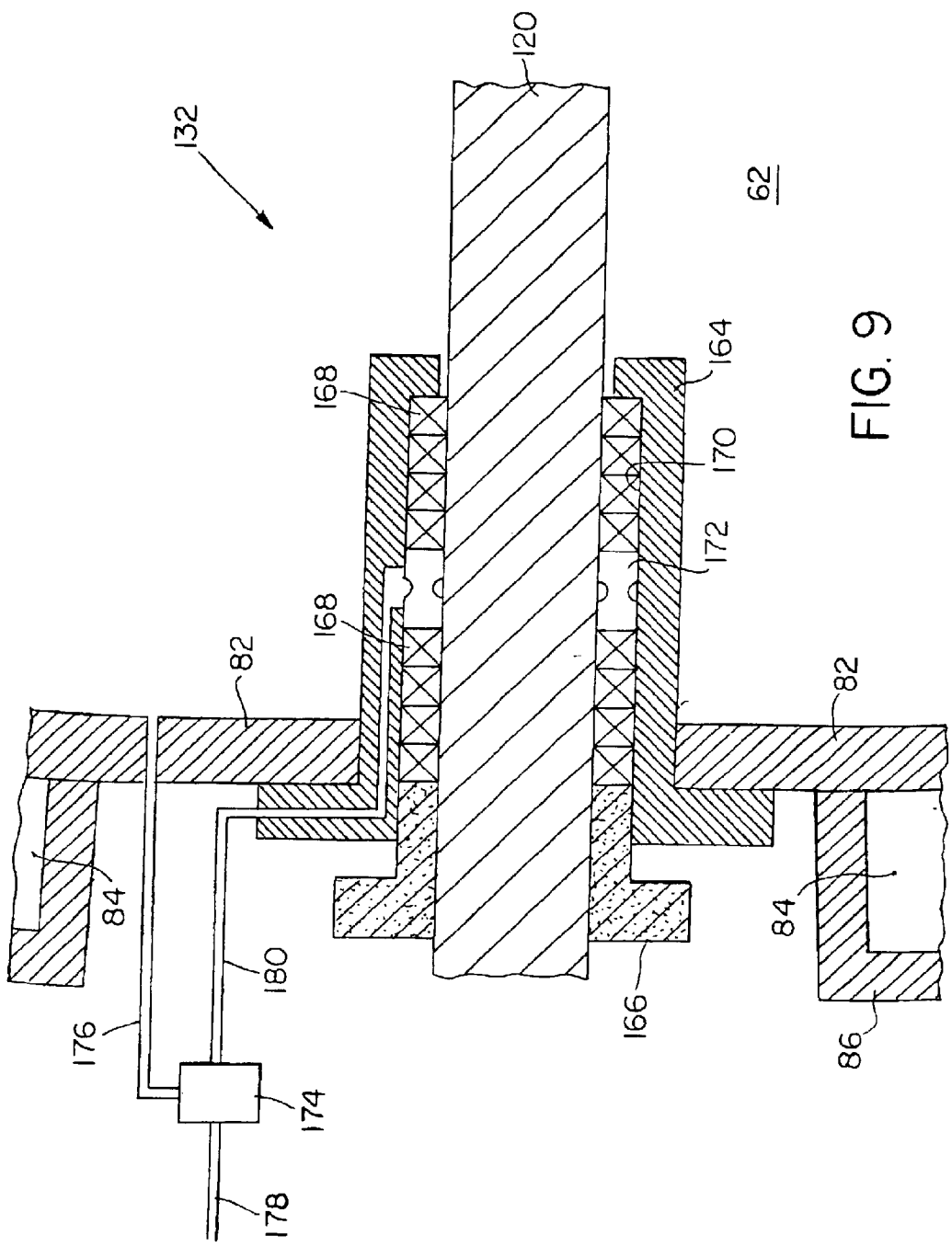
FIG. 9 is enlarged view of a seal for the shaft of the agitating mechanism.

One of the seals 132 for the shaft 120 of the agitating mechanism 68 is shown in FIG. 9. It is not desired for the biomedical waste including liquid and gas to leave the pressure vessel 62 prior to the completion of the sterilization of the waste. With a pressure differential between the pressure vessel 62 and the outside and the shaft 120 extending through an opening 130 in the pressure vessel 62 and the shaft 120 rotating, there would be a tendency for gas or liquid to escape from the pressure vessel. The seals 132 prevent the escape of fluid and gas from the pressure vessel 62.

The seal 132 has a sleeve 164 which in a preferred embodiment is made of stainless steel and is retained in the opening 130 in the pressure vessel by bolts. The seal 132 has a packing gland 166 for retaining a pair of shaft packings 168 in a channel 170 defined by the sleeve 164. A lantern ring 172 is interposed between the shaft packings 168 in the channel 170.

The seal 132 has a differential pressure controller 174, a mechanical device. The differential pressure controller 174 is connected to a pressure sensing line 176 which opens onto the pressure vessel 62 for sensing the pressure in the vessel 62. The differential pressure controller 174 in addition has a line 178 connected to a pressurized water source such as a city water system. The pressurized water source has to have a pressure higher than the pressure in the pressure vessel 62. The differential pressure controller 174 compares the pressure from line 178, the city water system, and the pressure sensing line 176. By varying the pressure from line 178, the differential pressure controller 174 applies a pressure through a line 180 to the lantern ring 172 using the city water which is 1–5 psi higher than the pressure sensed in the pressure sensing line 176.

The pressures on the shaft packing 168 between the opening to the pressure vessel 62 and the lantern ring 172 are therefore 1–5 psi higher than the pressure in the pressure vessel 62. If the shaft packing 168 becomes worn, there is a tendency for liquid or steam to leak past the shaft 120, the pressurized water, city water, will flow into the vessel 62, rather than the medical waste liquid and gases flowing out of the pressure vessel 62. A flow meter located on the line 180 to the lantern ring 172 can detect if the shaft packings 168 are worn by the flow of water. The packing gland 166 is tightened periodically to maintain the appropriate tension on the shaft packings 168 and the lantern ring 172. In the alternative, springs can be used to maintain the appropriate tension.

Figure 10:
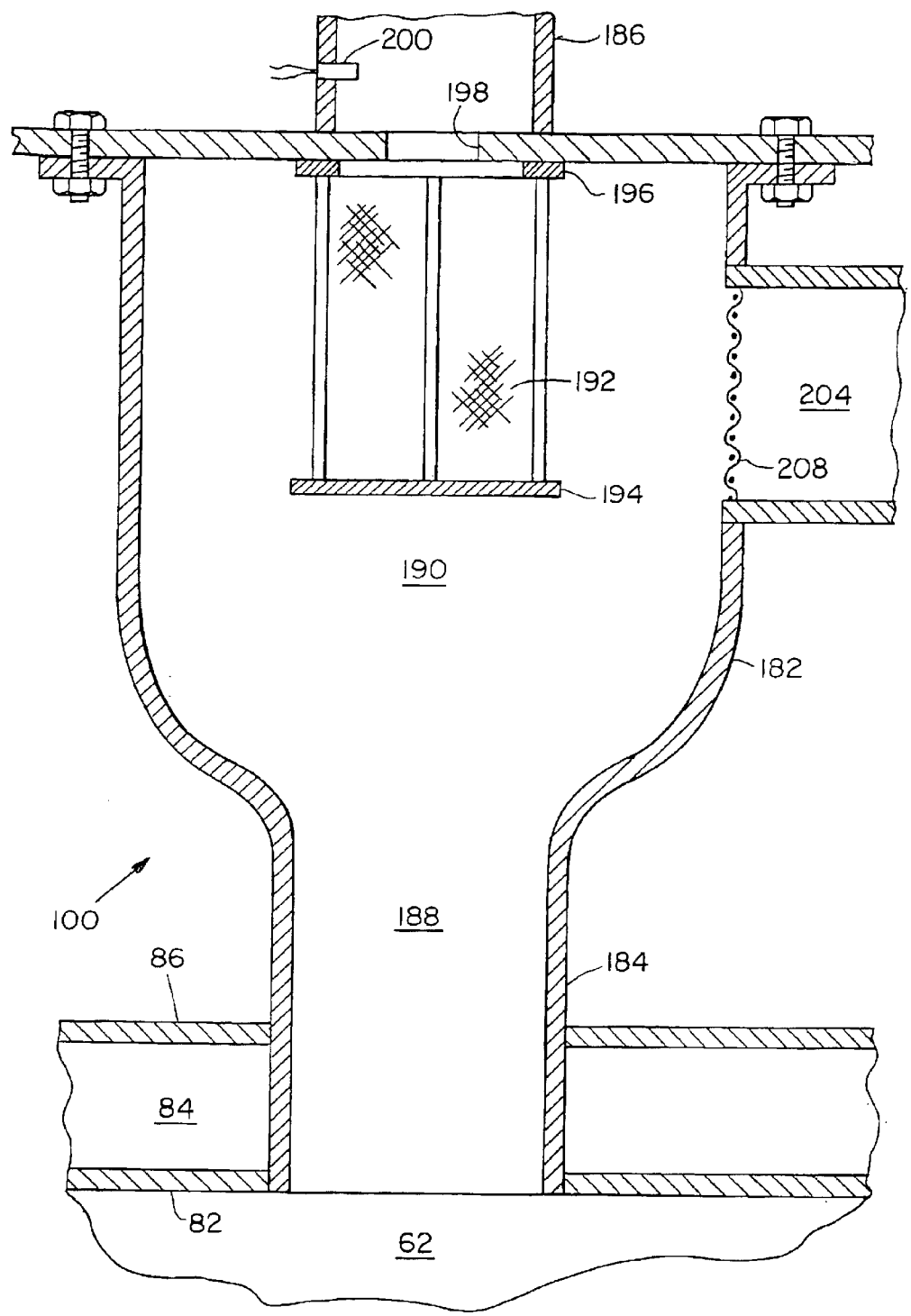
FIG. 10 is enlarged view of the vent.

The venting/filter system 100 has a venting bottle 182 which is connected to the pressure vessel 62 through a line 184 as seen in FIG. 10. The venting bottle 182 is also connected to a line 186 which is connected to the boiler through a steam line 88 and through two steam valves 90 and 96, as seen in FIG. 3, and connected to the vapor condensing system 72 through another steam valve 98, as seen in FIG. 3. Still referring to FIG. 10, the venting/filter system 100 has a narrow neck portion 188, which is connected to line 184, and an enlarged area 190. The velocity of the steam/gas is reduced when it enters the enlarged area 190 as explained below. Located within the enlarged area 190 is a cylindrical mesh 192 having a solid base 194 and an annular ring top 196 with an opening 198 to allow steam/gas to pass into the line 186. The cylindrical mesh 192 prevents small and lighter waste particles from entering the line to the vapor condensing system 72 and the steam valve 98. The concern is not with the particles being infectious medical waste, but with clogging the system.

The venting/filter system 100 has a flow measuring device or a pressure sensor device 200 upstream of the cylindrical mesh 192. In a preferred embodiment, the device is a pressure sensor device 200 located in the line 186. The device 200 is connected to the controller 74, as seen in FIG. 3, in order to sense when the mesh 192 has become clogged.

The venting bottle 182 of the venting/filter system 100 has an additional opening 204 for the negative air pressure device line 102. The line of the negative air pressure device 102 has a valve 206, as seen in FIG. 3, for limiting the flow through the line when it is not desired to create a back flow when loading. The opening 204 at the venting bottle 182 has a screen 208 to prevent small and lighter waste particles from settling in the line for the negative air pressure device 102 even though the line is closed when particles are typically in the venting bottle 182.

The operation of the processing apparatus 60 will be described with respect to FIG. 11. The waste, be it biomedical, another type of hazardous waste material or other waste where treatment is desired, is loaded into the pressure vessel 62 through the inlet port 76. In a preferred mode, a downward flow of air is induced in the inlet port 76 to prevent the escape of airborne emissions through the inlet port 76 during loading. The downward flow of air is created by the negative air pressure device 102. The controller 74 opens the valve 206 and turns on the fan 104 in the negative air pressure device 102 to pull air from the pressure vessel 62, therein creating a downward flow of air in the inlet port 76. The air pulled from the pressure vessel 62 is sent through the active charcoal filter or HEPA filter of the gas portion 118 of the vented emission treatment system 101, as seen in FIG. 3, to remove particles. A monitor can be located in the negative air pressure device 102 to ensure a low pressure is being created in the pressure vessel 62. An alarm located on the controller 74 can indicate when there is not a proper flow through the negative air pressure device 102.

In a preferred mode of operation, the agitating mechanism 68 is rotated by the driver 70 to enable the pressure vessel 62 to be loaded to a greater capacity. The shaft 120 in this preferred mode is rotated at a low rotational speed, for example at about 5 rpm, to reduce splashing of liquids through the inlet port 76 while the waste is being loaded. The waste, including the plastic bags and boxes in which other waste is stored, is broken into smaller components by the action of the rotating paddles 126.

Figure 12:
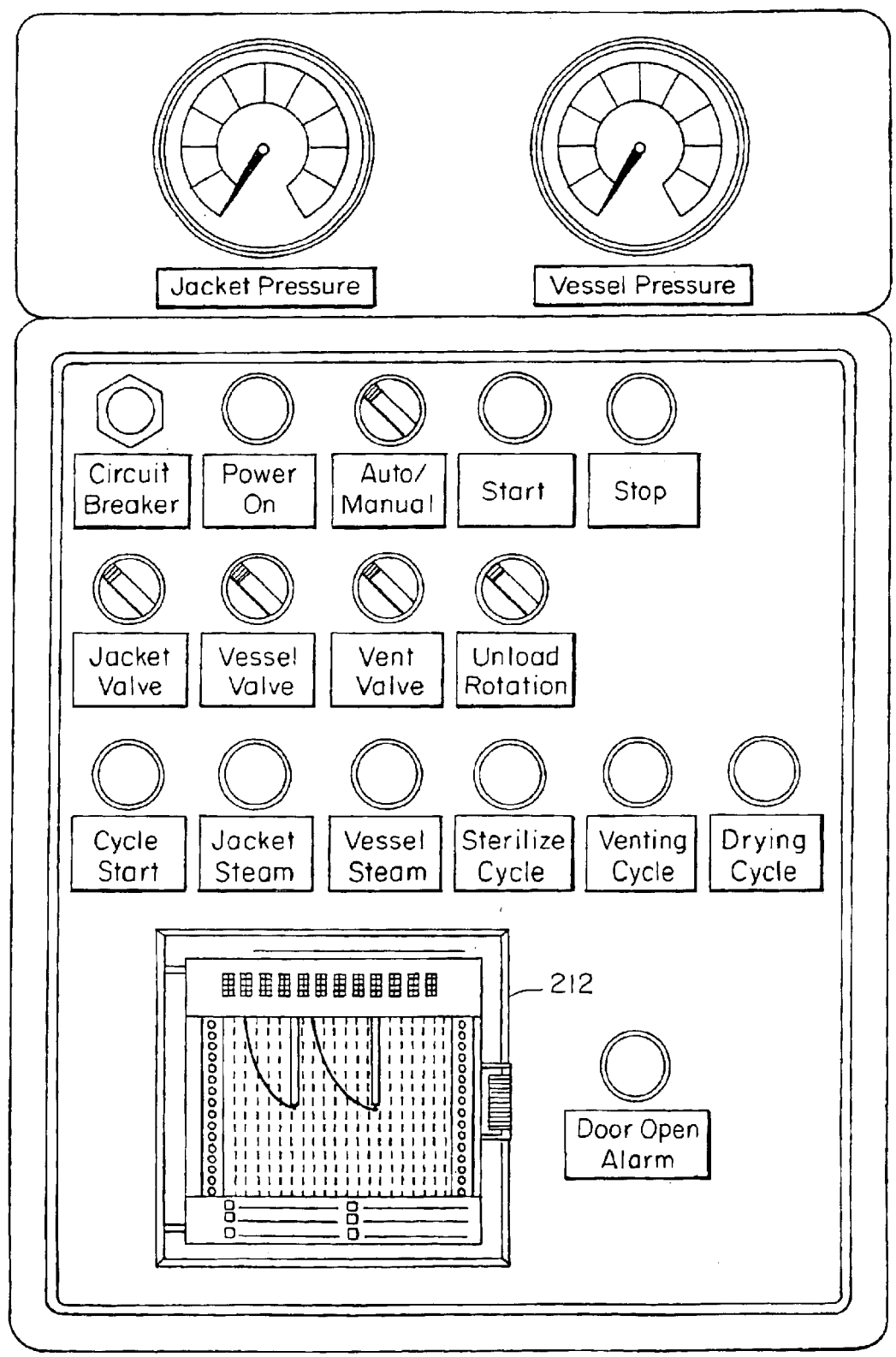
FIG. 12 is a schematic of a control panel.

The inlet port 76 is then hermetically sealed and the integrity of the seal between the pressure vessel 62 and the inlet port 76 and the outlet ports 78 is confirmed by conventional electrical interlocks. The negative air pressure device 102 is connected via the controller 74 to the loading door 76, such that the fan 104 is shut off and the valve 206 is closed when the loading door 76 is closed. With the pressure vessel 62 loaded and a start button, as seen in FIG. 12, pushed when in an automatic mode, the controller 74 has confirmed that the inlet port 76 and the outlet port 78 are closed and begins the sterilization process. A printer/recorder 212, as seen in FIG. 12, on the controller 74 is activated for a permanent recorder of the process. The first steam valve 90 and the second steam valve 92 are opened to allow steam to flow from the boiler to the space 84 of the steam jacket 64. The opening 148 allows trapped air to be bled. In a preferred embodiment, the steam is produced by a boiler not controlled by the controller 72 of the processing apparatus 60.

The controller 74 monitors the pressure through the pressure sensor 138 and the temperature through the temperature sensor 140. While the controller 74 is monitoring parameters and steam is entering the steam jacket 64, the shaft 120 and the paddles 126 of the agitating mechanism are rotated. In a preferred embodiment, the shaft 120 is suitably rotated at a speed of from about 5 to 50 rpm so that successive portions of the waste material contact the walls 82 of the pressure vessel 62 whereby the contents of the vessel 62 are heated substantially uniformly. Similar to the first embodiment, the heating cycle may be further enhanced by the provision of steam to the interior of the shaft 120.

The temperature is measured at the bottom of the pressure vessel 62, since any fluid located in the waste will drain to the bottom of the pressure vessel 62 when freed from the vial, box, bag or other container which contained it on entry into the pressure vessel 62. The fluid is not lifted by the paddles 126 of the agitating mechanism 68 and forms a large mass of liquid to heat at the bottom of vessel 62. This mass of fluid typically will take the longest to heat. Therefore the temperature sensor, thermocouple 140, typically measures the lowest temperature in the pressure vessel 62.

When the interior of the pressure vessel 10 and the waste material contained therein reaches a temperature of 100° C. (212 F.), moisture in the waste material is converted to steam, thereby increasing the pressure within the pressure vessel 62. Heating is continued until the temperature is in the range of from about 121° to 170° C. (250 to 338 F.) and a pressure in the range of from about 15 to 100 psig. It is not desired to raise the temperature so high as to chemically degrade the plastic. Therefore when certain plastics are contained in the waste, the temperature of the pressure vessel 62 should be limited to 132° C. (270° F.).

The combined action of the paddles 126 of the agitating mechanism 68 and the heat supplied by the steam jacket 64 cause the waste inside the pressure vessel 62 to further break down into smaller pieces. As bags and other containers are broken, any entrained air is released inside the pressure vessel 62. Accordingly, cold spots are substantially eliminated. Furthermore, the effects of the type of material, density of the material, batch volume and the degree to which the vessel is loaded are substantially reduced in the pressure vessel 62 and process of the present invention, especially as compared to a conventional autoclave.

Circulation of the smaller portions of waste material within the pressure vessel 62 allows for a more even heat distribution and a reduction of temperature gradients throughout the waste contained therein, ensuring that all portions of the waste material are exposed to the appropriate temperature and pressure for a period of time sufficient to achieve sterilization of the material.

There is generally sufficient moisture in biomedical waste to pressurize the pressure vessel 62 to the desired operating pressure and temperature. However, if the moisture content of the waste material is unusually low, for example less than 10%, there may be insufficient moisture to pressurize the pressure vessel 10. A situation wherein the moisture content is insufficient is detected by the controller 74 by monitoring the pressure sensor 138 and the temperature sensor 140. If there is insufficient moisture, the pressure inside the pressure vessel 62 does not increase proportional with an increase in temperature and the desired combination of temperature and pressure to effect sterilization may not be realized. This may be overcome by injecting high pressure steam. The controller 74 opens the steam valves 90 and 96 so that the steam from the boiler, the jacket supply steam, is placed directly into the pressure vessel 62 through the venting/filter system 100 to increase the moisture content of the pressure vessel 62 and the waste. In this way, the moisture content inside the pressure vessel 62 is not unduly increased. Alternatively, water may be added to the pressure vessel 10 during the loading step. However, this method is not as efficient and not as easy to monitor.

Figure 13:
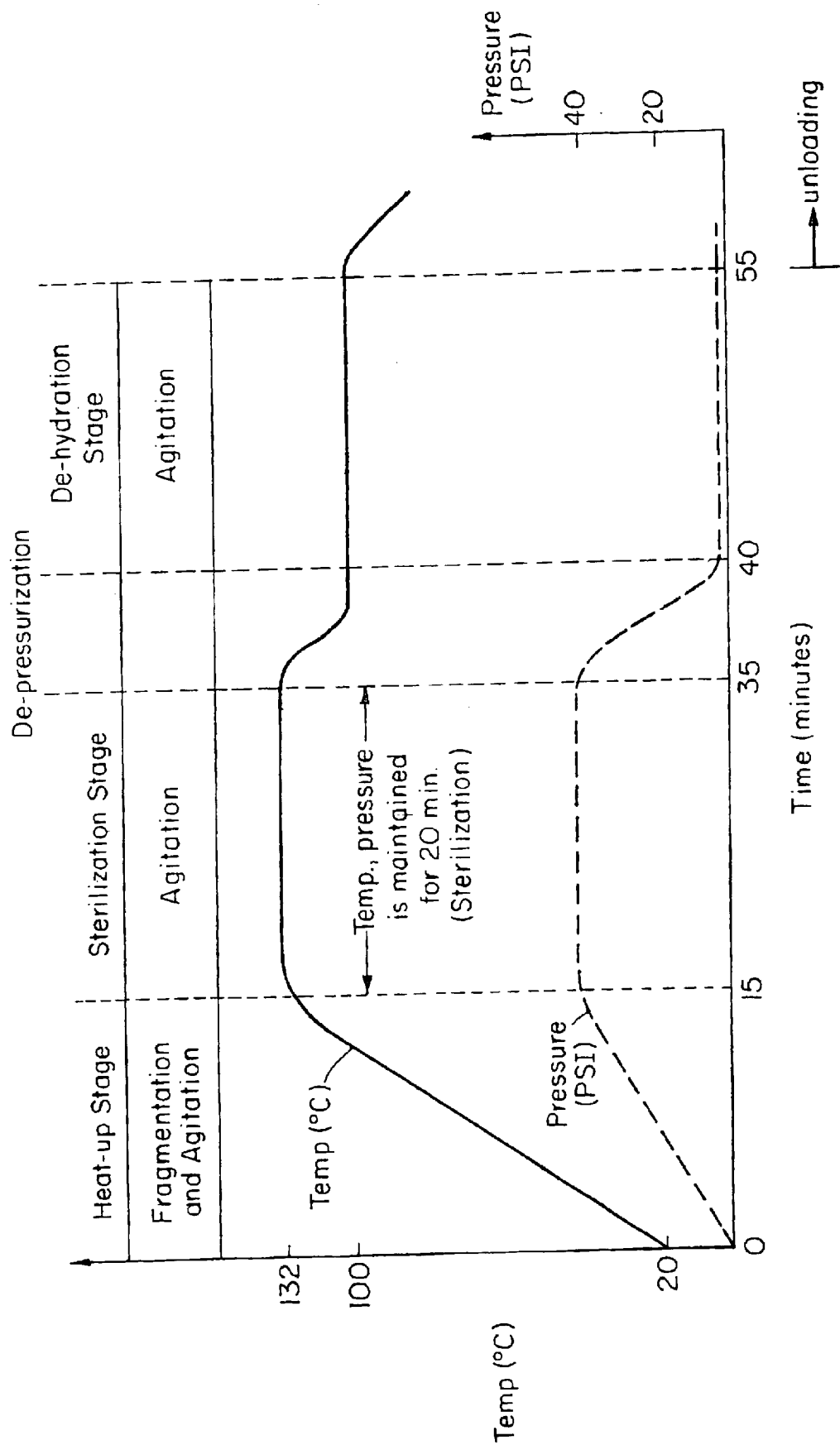
FIG. 13 is a chart of an example of temperature and pressure relative to time in the pressure vessel and symbolic of the output from the controller.

After the desired treatment time at proper pressure and temperature, the pressure vessel 62 is de-pressurized to atmospheric pressure by the controller 74. The desired treatment time is dependent on the temperature and pressure in the pressure vessel 62. The following is a table of times for a preferred embodiment for the temperature and pressure given. The temperature of 170° C. is typically used for large animals such as described in the next embodiment. FIG. 13 shows an example of temperature and pressure in the pressure vessel 62 during the various stages of the sterilization process and a typical time of each process.

| Temperature (° C.) | Pressure (PSI) | Time (Minutes) (Sterilization Stage) |
|---|---|---|
| 121 | 15 | 30 |
| 132 | 38 | 15 |
| 170 | 100 | ≦15 |

The controller 74 de-pressurizes the pressure vessel 62 by opening the steam valve 98 which vents the steam and gas from the pressure vessel 62 through the venting/filter system 100 to the vapor condensing system 72. The controller 74 turns on the flow of water in the cooling system 108 and regulates the valve 114 through the controller 116 allowing only enough steam and gas from the pressure vessel 62 as the cooling system 108 can cool. The output temperature, as monitored by the temperature sensor 112, determines how much steam and gas the cooling system 108 can cool. Those gases in the vapor condensing system 72 which are not condensible are vented through the gas portion 118 of the vapor condensing system 72. The gas portion 118 has an active charcoal filter or a HEPA filter at the top of the stack through which the gases pass in order to remove odor. All the steam, moisture or gas has been retained in the pressure vessel for the designated temperature and time period and therefore is treated prior to discharging and can be treated as normal waste.

The temperature in the pressure vessel 62 is kept in the range of 121° to 132° C. (250° to 270° F.) to achieve sterilization without having chemical breakdown of the plastics. Certain plastics such as polyvinyl chloride can give out a hazardous gas if heated to a high temperature.

While the pressure vessel 62 is being depressurized, the venting/filtering system is ensuring that no small or lighter waste particles enter the line to the vapor condensing system 72 and the steam valve 98. The concern is not with the particles being medical waste, but that the particles may clog the system. On initiating the venting, there will be a strong velocity through the line 184 from the pressure vessel 62 to the venting bottle 182, because of the increased pressure in the pressure vessel 62. Any waste particles that are lifted by the increased velocity will be slowed down in the enlarged area 190 of the venting bottle 182. Most waste particles will gravitate back through the line 184 into the pressure vessel 62. Smaller and lighter waste particles will be prevented from exiting the venting bottle 182 by the cylindrical mesh 192. Therefore, only clean steam and gases will exit through the opening 198 and into the line 186. The controller 74 will be monitoring to determine if the cylindrical mesh 192 is clogged. In a preferred embodiment, the controller 74 monitors by comparing the pressure in the line 186 to the pressure in the pressure vessel 62 by comparing the pressure sensor 200 to the pressure sensor 138. When the controller 74 determines that the flow is being blocked through the mesh, by a large pressure differential between the pressure in the line 186 and the pressure in the pressure vessel 62, the controller 74 opens the steam valve 96 so that a shot of live steam is sent into the pressure vessel 62. The force of the steam is sufficient to clean the particles off of the cylindrical mesh 192. The steam valve 90 should already be open, but if not the controller 74 will also open that valve.

Preferably, the pressure vessel 10 is depressurized while heating is continued by maintaining steam input to the steam jacket 16. In this way, substantially all of the moisture in the waste material will evaporate. The decrease in pressure results in flashing a large portion of liquid to vapor. While the volume of the waste is reduced during the entire process of the present invention, the reduced water content during the de-pressurization step act to further reduce the volume of the treated waste. Depending on the moisture content, density and other characteristics of the waste, it is possible to reduce the volume to about one-fifth of the original volume of waste material. The reduced moisture content represents a decrease in the weight of the treated waste in addition to reduced landfill and transportation costs.

Both during the sterilization, and the dehydration stages, the agitating mechanism 68 is moving the waste. During the de-pressurization stage, the controller 74 stops the agitating mechanism 68 in order to minimize the amount of particles that are pulled into the venting bottle 182 of the venting/filter system 100. When the pressure in the pressure vessel 62 gets down to 2 psig, in a preferred embodiment, the controller 74 starts the shaft 120 of the agitating mechanism 68 by powering the electric motor 122. The blade 152 is the front facing blade on each of the paddles 126 as the shaft rotates in the mixing direction, the clockwise direction as shown in FIG. 6, to move the waste in a series of planes perpendicular to the shaft 120. The agitating mechanism 68 is mechanically breaking the waste into smaller components and facilitating uniform heating of the waste.

The knife edges 158 mounted on the upper half of the wall 82 of the pressure vessels interact with the blades 152 and 154 of the paddles 126 to reduce or eliminate tangling of waste on the paddles 126. As the paddle 126 rotates it may pick up waste which gets tied up or wound around the paddle 126 and does not drop back into the accumulation of waste located in the lower portion of the pressure vessel 62 as the paddle 126, or at least the blades 152 and 154, rises above the top of the accumulation of waste in the pressure vessel 62. Typical waste that would get wound around the paddle 126 includes cloth bandages, sheets, rubber hoses and other items that are flexible and of large length to width ratio. The knife edge 158 cut those items that are caught on the blades 152 and 154 of the paddle 126 and are brought into engagement with the knife edge 158.

When the controller 74 determines that the de-hydration stage is completed either by a timer or in a preferred embodiment by monitoring the temperature in the pressure vessel 62 and noting an upswing in temperature, the controller 74 will stop the agitating mechanism 68 and closes the valves 90 and 92 to shut the steam to the steam jacket 64. The controller 74 then will signal to the user that the unloading door 78 can be opened. With the outlet port, unloading door 78 opened, the controller 74 will initiate the agitating mechanism 68 in the opposite direction. The other blade 154, which is angled relative to the shaft 120, is the facing blade and engages the waste as the shaft 120 rotates in a counter-clockwise direction as seen in FIG. 6, therein moving the waste towards the unloading door 78.

The knife edges 158 likewise interact with the blades 152 and 154 of the paddles 126 to reduce or eliminate tangling of waste on the paddles 126. In that the waste is being moved to one end of the pressure vessel 62 there is an increased likelihood of tangling. Therefore, the paddles 126 which are near the ends of the pressure vessel 62 are adapted to interact with a multiplicity of knife edges 158. The scrapers assist in removing the waste from the end walls of the pressure vessel 10. The treated waste material is thus emitted from the vessel 10.

Figure 11A:
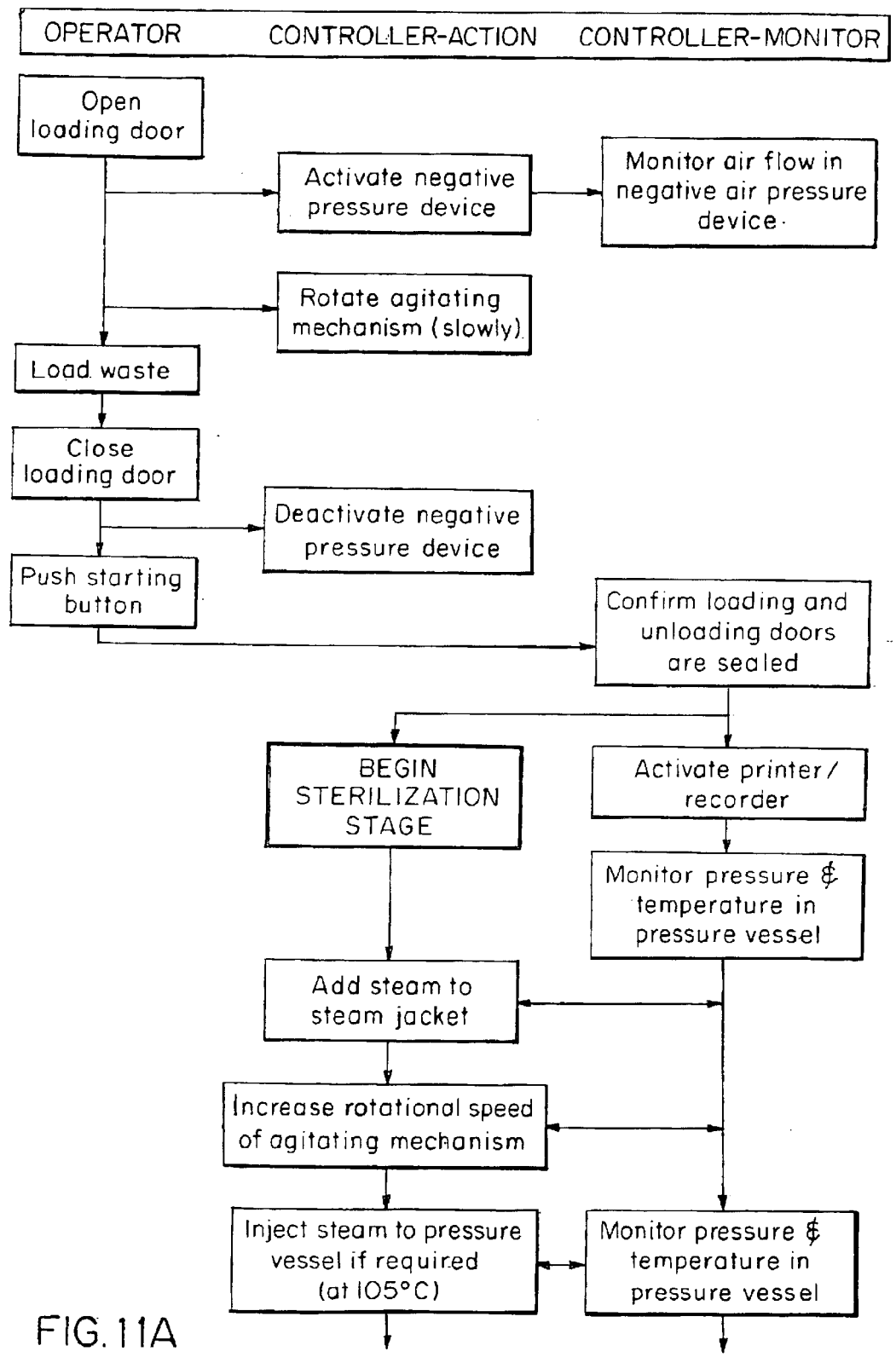
FIGS. 11A–11C is a flow chart of a control process.
Figure 11B:
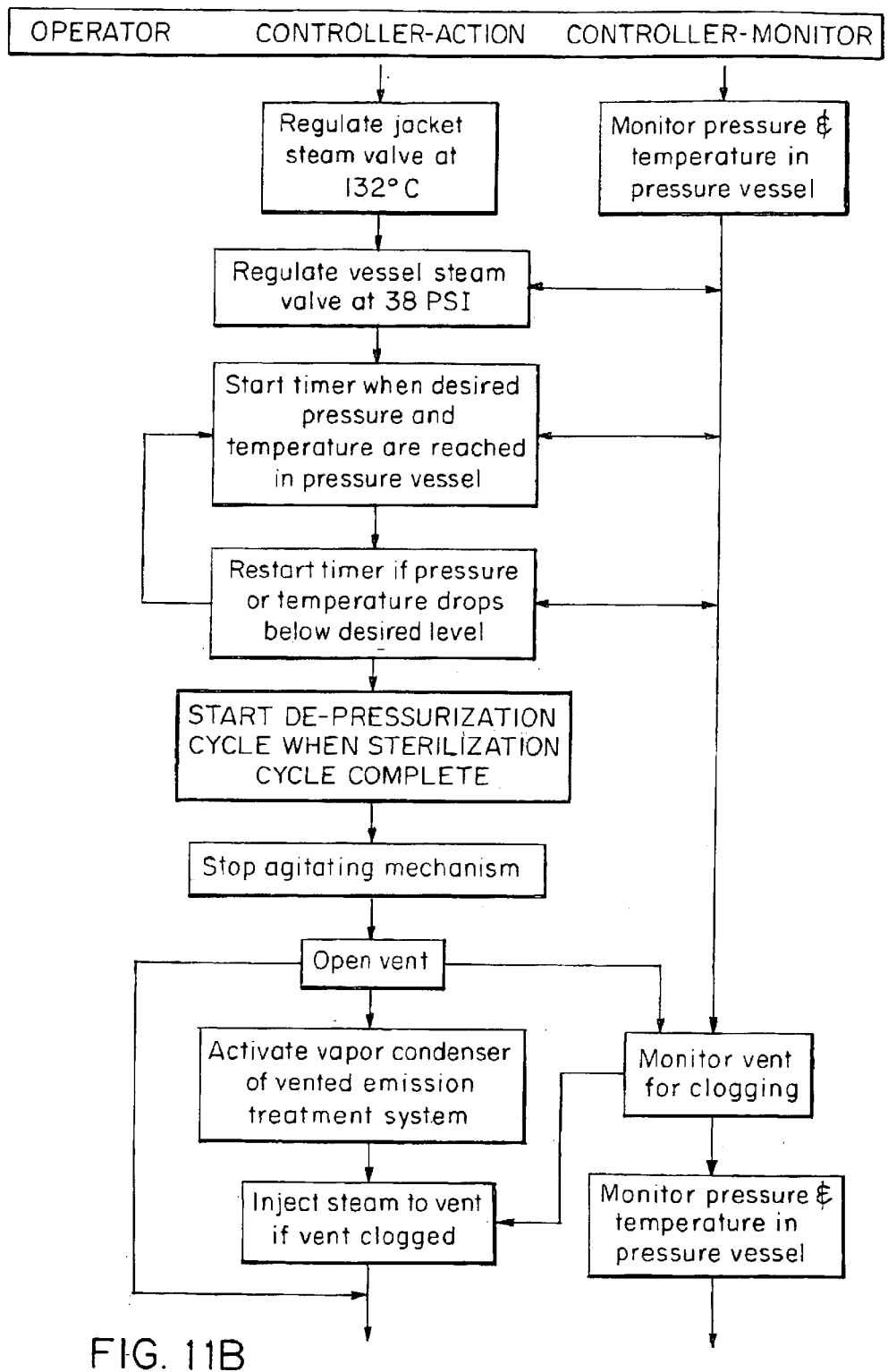
Figure 11C:
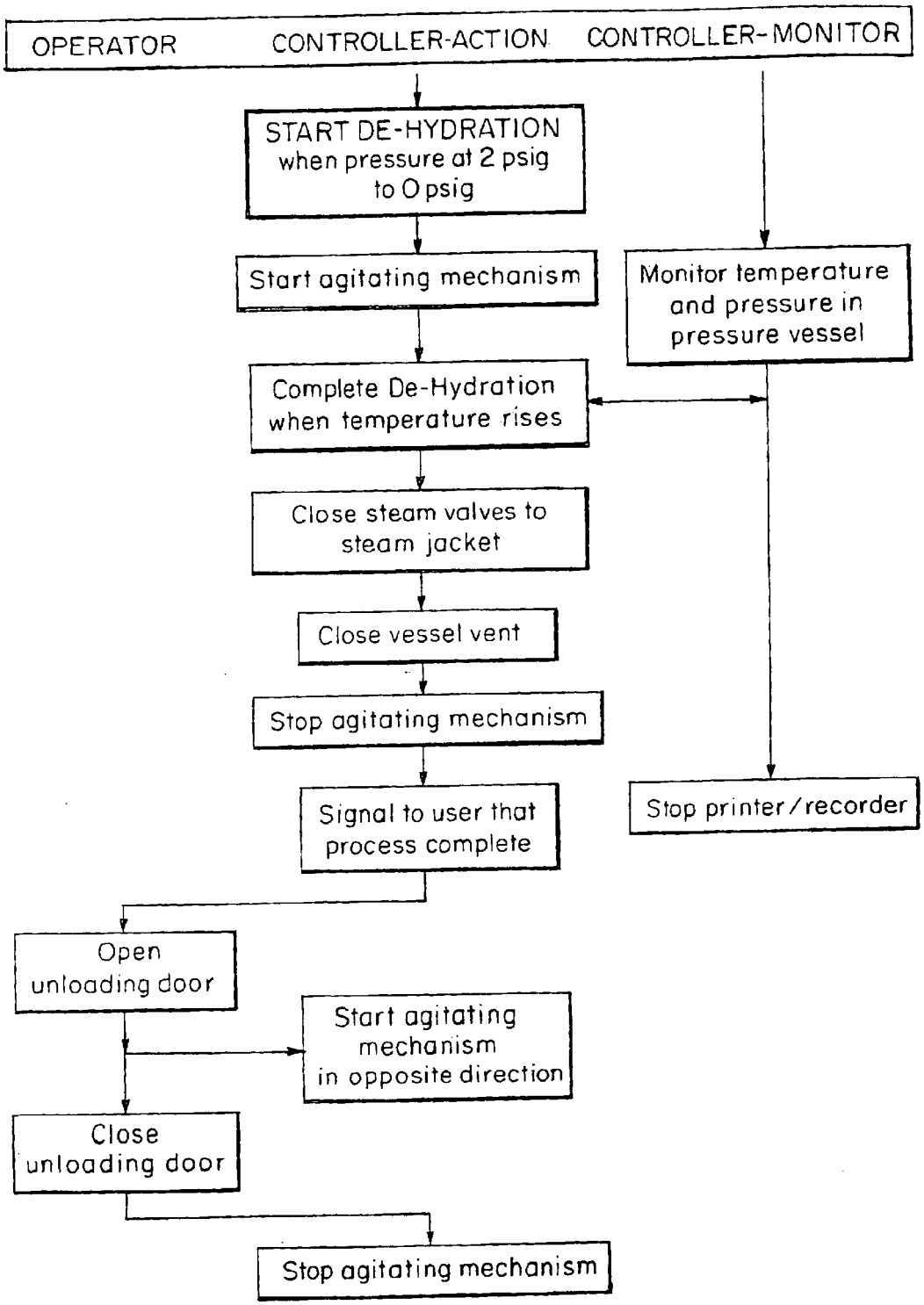

The waste drops from the pressure vessel 62 into the shredder 66, where it is further broken up and shredded. The treated shredded waste can be shipped away as declassified municipal waste. The controller 74 has produced a chart indicating parameters including pressure and temperature in the pressure vessel versus time. The temperatures and pressures given in FIGS. 11A–C are nominal ideal for a particular preferred embodiment. It is recognized that the temperature, pressure and revolutions per minute could vary.

While generally transparent to the user, the controller 74 is monitoring the seal 132 to ensure that there is no leakage. The seals 132 have the differential pressure controllers 174 which compare the pressure from line 178 and the pressure sensing line 176 and applies a pressure through a line 180 to the lantern ring 172 using the city water which is 1–5 psi higher than the pressure sensed in the pressure sensing line 176. The pressures on the shaft packing 168 between the opening to the pressure vessel 62 and the lantern ring 172 are therefore 1–5 psi higher than the pressure in the pressure vessel 62.

Figure 14:
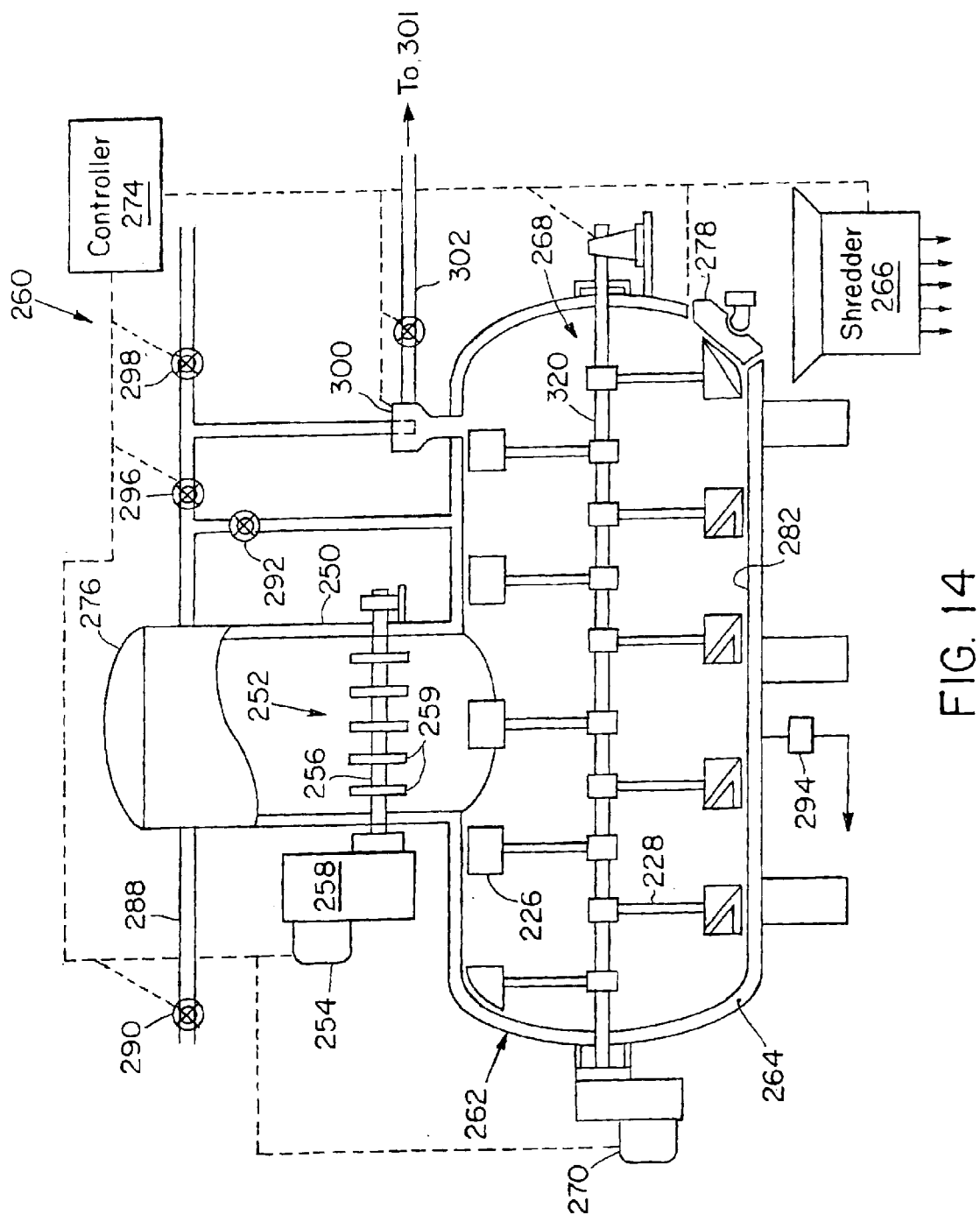
FIG. 14 is a schematic view of an alternative apparatus having a carcass loading door.

An alternative embodiment of a processing apparatus 260 is shown in FIG. 14. The processing apparatus 260, similar to the previous embodiment, has a pressure vessel 262, a heating jacket 264 substantially surrounding the pressure vessel 262, a shredder 266, an agitating mechanism 268 with a driver 270, a vapor condensing system, not seen in FIG. 14, and a controller 274. The pressure vessel 262 has an inlet port, a loading door 276, and an outlet port, an unloading door 278.

Similar to the previous embodiment, the loading door 276 is for receiving the untreated waste. However, in contrast to the previous embodiment, the loading door 276 is spaced from the cylindrical pressure vessel 262 by an extended neck 280. In addition, the loading door 276 is of the size that a carcass of an animal, such as a horse, can be placed in the extended neck. The extended neck 250 has a grinder 252 with a driver 254. The waste does not require any pre-processing treatment prior to placing through the loading door 276.

The pressure vessel 262 is substantially similar to the previous embodiment with the addition of the extended neck 250. The heating jacket 264 surrounds the pressure vessel 262 and can also surround the extended neck 250. The heating jacket 264 is capable of transferring heat to the exterior walls 282 of the pressure vessel 262, including the extended neck 250 if desired. In a preferred embodiment, the heating jacket 264 is a steam jacket. The heating jacket 264 is covered with an insulating material such that the heat is direct to the pressure vessel and not to the surrounding environment, such as a waste treatment room.

The steam flows from a boiler in a steam line 288 through a first steam valve 290 and a second steam valve 292, which can operate manually and connect to the controller 274 to operate automatically, into the jacket. The steam is not in direct contact with the waste being treated in the pressure vessel 262. Any steam which condenses inside the steam jacket 264 is drained via a steam trap 294 for reheating in the boiler before being returned to the steam jacket 264.

In addition, the steam line 288 is connected to the pressure vessel 262 via a third steam valve 296 to allow the addition of steam to the pressure vessel 262 if needed, for reasons given above in the previous embodiment. It is not likely that moisture will need to be added when the waste consists of a large animal in excess of 100 lbs and in many applications over 500 lbs. The pressure vessel 262 is also connected to the liquid/vapor handling system through a fourth steam valve 298. As in the previous embodiment, the steam valves are controlled by the controller 274.

The steam line 288 is connected to the pressure vessel 262, in addition to through the third steam valve 296, through a venting/filter system 300 attached to the pressure vessel. The venting/filter system 300 limits what particles leave the pressure vessel towards the vapor condensing system, similar to the previous embodiment.

In addition to the line that carries vapor from the pressure vessel 262 to the vapor condensing system 272, a line for the negative air pressure device 302 extends from the venting/filter system 300 to a vapor portion of a vented emission treatment system 301.

The vented emission treatment system, while not shown in FIG. 14, is similar to that described with respect to FIG. 3 in the previous embodiments.

The agitating mechanism 268 has a shaft 320 which extends longitudinally through the pressure vessel 262 and is connected to the driver 270, an electric motor in a preferred embodiment. The agitating mechanism 268 has a plurality of paddles 226 which are located in proximity to the walls 382 of the pressure vessel 262 and spaced from the shaft 220 each by an arm 228. The paddles are directional scoop blades as in the previous embodiment. The agitating mechanism 268 has a seal similar to that described in FIG. 9 with the previous embodiment.

The grinder 252 is located in the extended neck 250 of the pressure vessel 262. The grinder 252 has a series of shafts 256 which extend longitudinally through the extended neck 250 and are connected to the driver 254 through a gearing arrangement 258. The grinder 252 has a plurality of teeth 259 which intermesh to roughly grind the waste. By breaking down the carcass, the process is sped up by allowing the temperature in the pressure vessel 262 to achieve the uniform desired temperature more quickly. The grinder 252 has seals similar to those described with respect to the agitating mechanisms 68 and 268. In loads which contains only a carcass(es) it may be desirable to have the pressure vessel 262 at temperature of 170° C. to speed the breakdown of the carcass.

The shredder 266 is located in proximity to the unloading door 278 of the pressure vessel 262. The shredder 266 takes the waste which has been treated in the pressure vessel 262, and further breaks up and shreds the waste into smaller pieces. The shredder 266 is not required to process the biomedical waste to result in sterile waste.

The entire processing apparatus is controlled by the controller 274. The controller 274 takes inputs from monitors and sensors, and the controller 274 administers the process and records data. The controller 274 is similar to the previous embodiment, but in addition, it can control the grinder 252.

Figure 15:
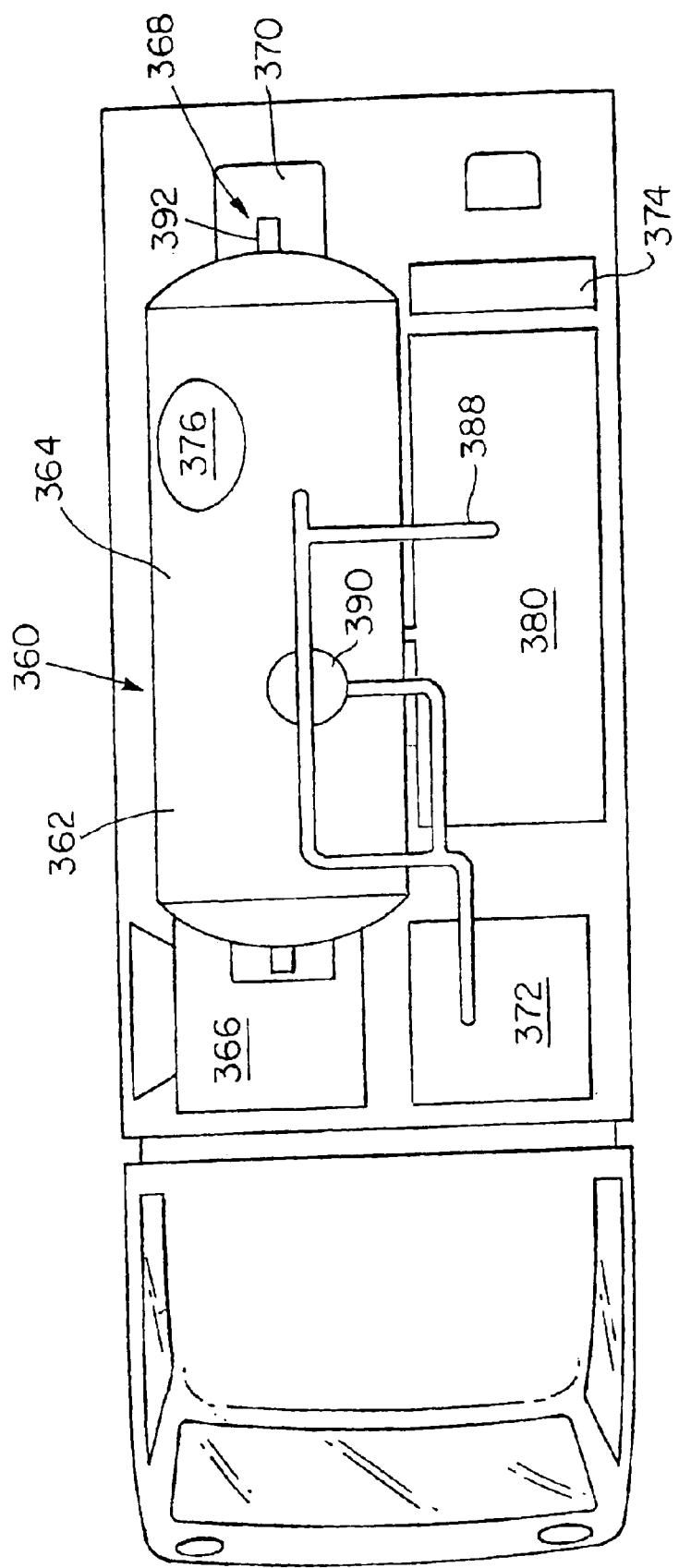
FIG. 15 is another alternative embodiment with a mobile apparatus.

In situations where untreated biomedical waste is located distant from a waste treatment or processing facility, a mobile processing apparatus 360, as seen in FIG. 15 could be brought to the location. The mobile processing apparatus 360 could also be useful in cleaning up accidental spills on highways, at industrial and/or commercial sites, or at medical treatment facilities. The mobile processing apparatus 360 is a vehicle equipped with a pressure vessel 362, a heating jacket 364 substantially surrounding the pressure vessel 362, a shredder 366, an agitating mechanism 368 with a driver 370, a vapor condensing system 372, a heat generator 380 and a controller 374. The pressure vessel 362 has an inlet port, a loading door 376, and an outlet port, an unloading door, located above a portion of the shredder 366. The loading door 376 is for receiving the untreated waste. The waste does not require any pre-processing treatment.

The pressure vessel 362 is substantially a cylindrical tube with a domed ends. The pressure vessel 362 is surrounded by the heating jacket 364 which is capable of transferring heat to the exterior walls 382 of the pressure vessel 362. The heating jacket 364 can be a space defined by the exterior walls of the pressure vessel 362 and an outer exterior wall; this double walled vessel is capable of containing a heated liquid or gas An alternative embodiment of the heating jacket 364 is heated elements embedded in a material, such as heating wires in an electrically insulative but thermally conductive material. The heating jacket 364 can be covered with an insulating material such that the heat is direct to the pressure vessel.

In a preferred embodiment, the heating jacket 364 is a steam jacket and the heat generator 380 is a boiler. The steam flows from the boiler 380 in a steam line 388 through a first steam valve and a second steam valve, which can operate manually and is connected to the controller 374 to operate automatically, into the jacket. The steam is not in direct contact with the waste being treated in the pressure vessel 362. Any steam which condenses inside the steam jacket 364 is drained via a steam trap 394 for reheating in the boiler before being returned to the steam jacket 364.

The steam line 388 is in addition connected to the pressure vessel 362 via a third steam valve to allow the addition of steam to the pressure vessel 362 if needed, similar to that described in the previous embodiments. The pressure vessel 362 is also, connected to the liquid/vapor handling system 372 through a fourth steam valve. The steam valves are controlled by the controller 374.

The steam line is connected to the pressure vessel 362, in addition to through the third steam valve, through a venting/filter system 390 attached to the pressure vessel 362. The venting/filter system 390 limits what particles leave the pressure vessel towards the vapor condensing system 372, as described above with respect to previous embodiments and FIG. 10.

In addition to the line that carries vapor from the pressure vessel 362 to the vapor condensing system 372, a second line extends from the venting/filter system 390 to the vapor condensing system 372. The line is part of a negative air pressure device for creating a low pressure to draw air into the pressure vessel 362 during filling.

The vapor condensing system 372 receives the steam, moisture or gas that is drawn away or forced away from the pressure vessel through the venting/filter system 390. The vapor condensing system 372 has a cooling system which in a preferred embodiment is connected to a water system. The steam, moisture or gas which leaves the pressure vessel 362 is cooled and turned back into a liquid by the vapor condensing system 372 by the water from the water system flashing the steam into liquid in the cooling system prior to placing the steam, which is now liquid, into a sewer system or holding tank. The vapor condensing system 372 can have a temperature sensor which monitors the temperature of the water leaving the cooling system. The temperature sensor is connected to a valve in the line from the pressure vessel through a controller. The valve limits the flow of steam into the cooling system so that the water from the water system is capable of keeping the temperature of the liquid entering the sewer system below 65.5° C. (150° F.). The controller can be a portion of the controller 374.

Those gases in the vapor condensing system 372 which are not compressible are vented through a vapor portion of the vapor condensing system 372. The vapor portion is connected to the cooling system through a vent pipe. The vapor portion has an active charcoal filter or a HEPA filter at the top of the stack through which the gases pass in order to remove odor. All the steam, moisture or gas has been retained in the pressure vessel for the designated temperature and time period and therefore treated prior to discharging and can be treated as normal waste.

The agitating mechanism 368 has a shaft 392 which extends longitudinally through the pressure vessel 362 and is connected to the driver 370. The driver 370 in a preferred embodiment has a diesel engine which rotates the shaft 392 via a belt. The agitating mechanism 368 has a plurality of paddles which are located in proximity to the walls of the pressure vessel and spaced from the shaft each by an arm.

The shredder 366 is located in proximity to the unloading door of the pressure vessel 362. The shredder 366 takes the waste which has been treated in the pressure vessel 362, and further breaks up and shreds the waste into smaller pieces.

The entire processing apparatus is controlled by the controller 374 which takes inputs from monitors and sensors, and the controller 374 administers the process and records data. The controller 374 is similar to those explained above, but in addition controls the heat generator 380.

In accordance with the present invention, it is possible to provide economic and effective waste treatment at individual medical treatment facilities. It may be feasible to utilize existing steam plants at these medical treatment facilities as an energy source. Furthermore, the cost and potential hazards associated with the transport of biomedical waste would be eliminated. The waste treatment process and apparatus of the present invention provides economic and effective treatment of biomedical and/or other hazardous waste. The waste is broken down and tumbled against the heated walls of the pressure vessel thereby maximizing heat transfer to the waste, especially as compared to conventional treatment in an autoclave. There are substantially no toxic or odorous gas emissions and only sterile treated water is released to sanitary sewers. Furthermore, energy consumption is reduced and treatment facilities are relatively inexpensive to construct and operate.

Figure 16:
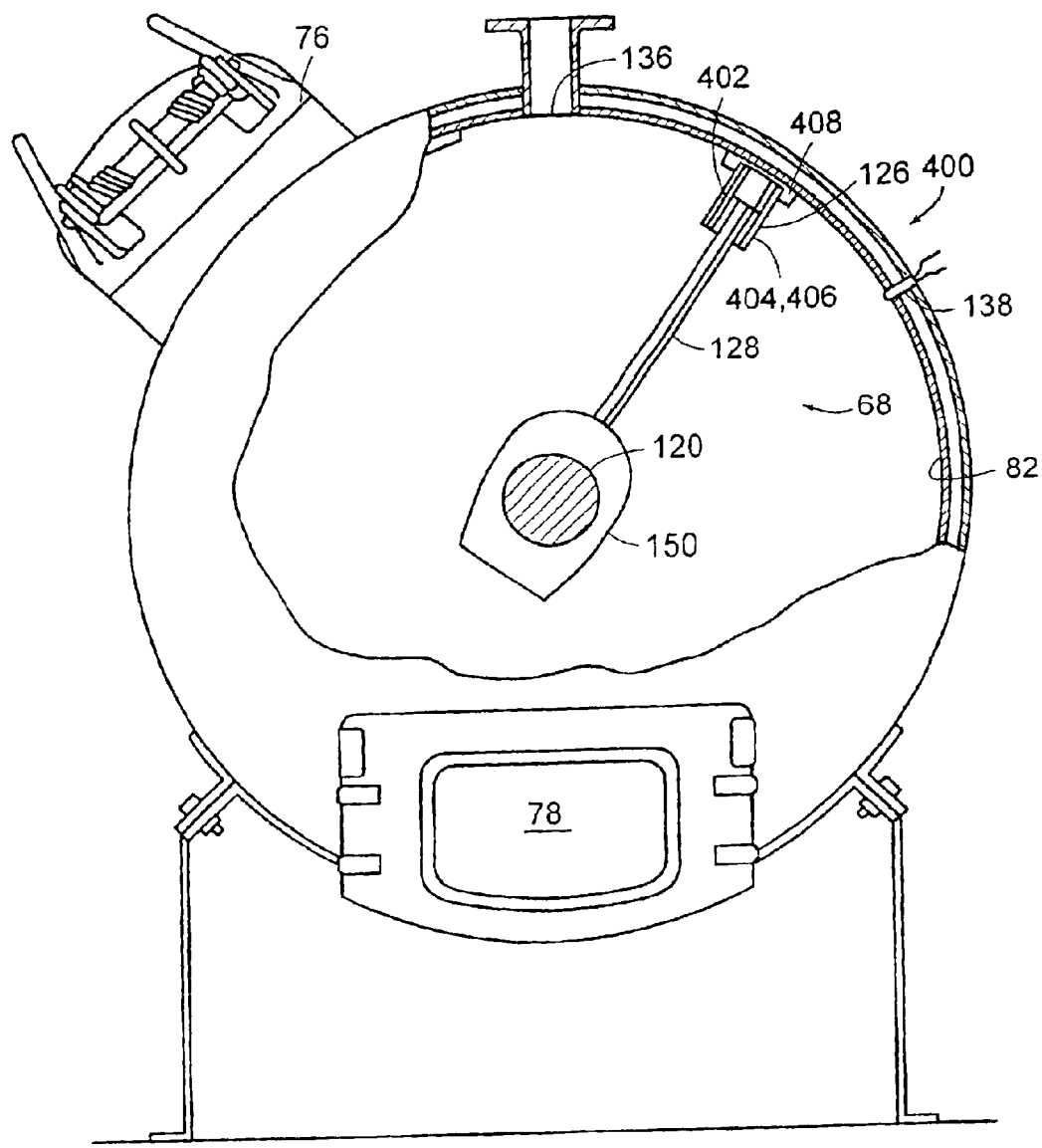
FIG. 16 is an end view of an alternative pressure vessel with a portion broken away showing the interior including paddles.

Referring to FIG. 16, an alternative pressure vessel 400 is shown with a cylindrical shell with domed ends to create the closed vessel. Similar to the previous pressure vessel, the pressure vessel 400 has a shaft 120 of an agitating mechanism 68 extending along vessel 400. A plurality of paddles 126 are mounted to the shaft 120 by an arm or rod 128 extending from a clamp 150 bolted to the shaft 120 to the paddle 126. Each paddle 126 has at least one blade 402. In one embodiment, the paddle has a pair of blades. The blades are joined at one edge 404. One blade is parallel to the shaft 120 and generally moves the waste in a series of planes perpendicular to the shaft 120 as the shaft 120 rotates in one direction. The other blade is angled relative to the shaft 120 such that the face of the blade opens towards the end of the pressure vessel 400 that has the unloading door 78. Therefore when the shaft 120 is rotated in the opposite direction, for example counter-clockwise in FIG. 16, the waste is moved towards the unloading door 78.

The blades have a knife edge 406 on their edges. The knife edge 406 interacts with a series of blocks 408 carried on the walls 82 of the pressure vessel 400, and on the upper half of the pressure vessel 400 in one embodiment. The blocks 408 hinder rotation of the waste to allow the blades to cut the waste.

Figure 17:
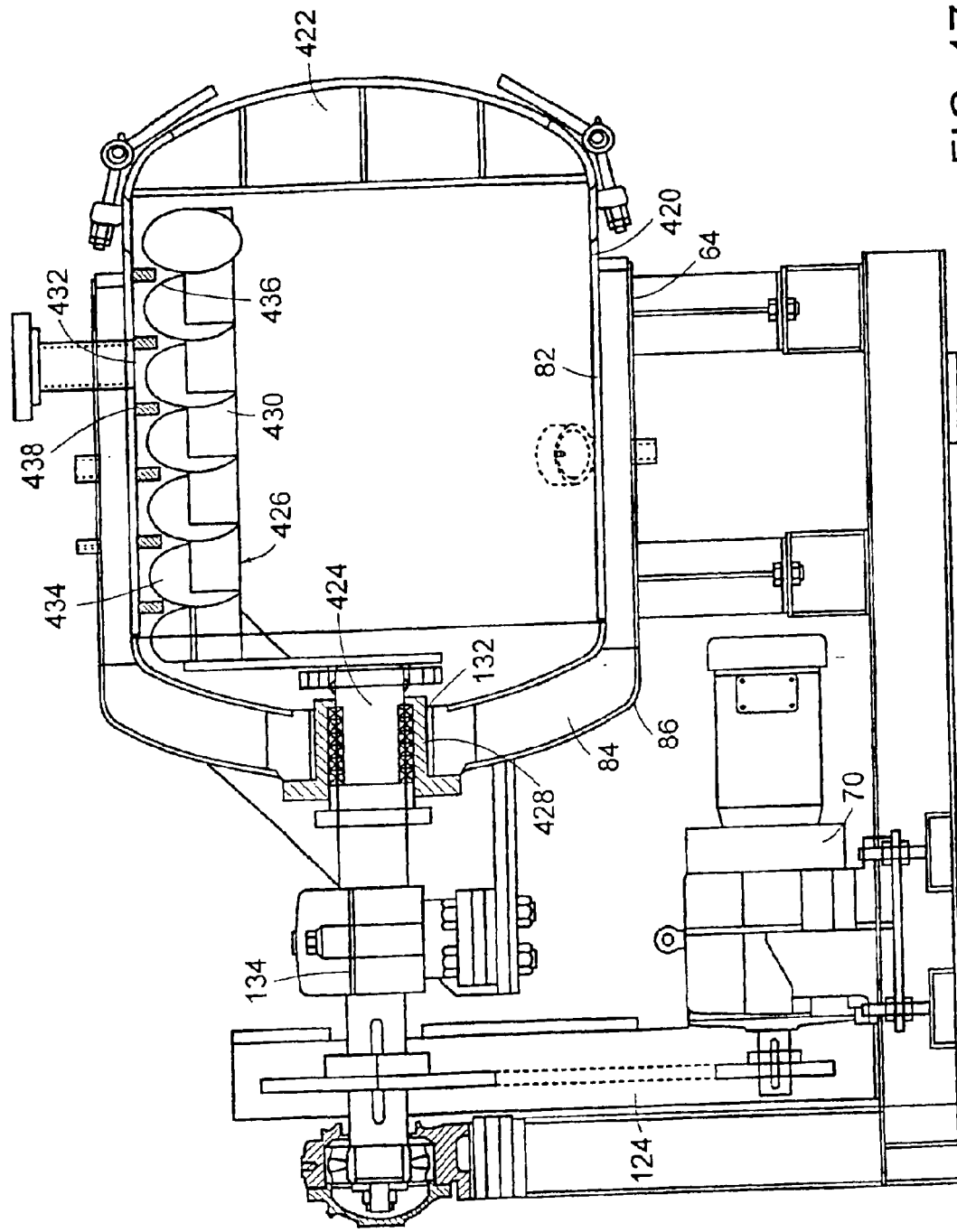
FIG. 17 is a side view of alternative pressure vessel according to the invention with portions shown in section.

Referring to FIG. 17, an alternative pressure vessel 420 is substantially a cylindrical shell with domed ends to create the closed vessel. While the operating pressure is not considered extremely high pressure, it is desired in the preferred embodiment to minimize the openings in the pressure vessel 420. In the embodiment, the pressure vessel 420 has a single port 422 for loading and unloading of waste. The shaft 424 of the agitating mechanism 426 extends through a single opening 428. The shaft 424 extends through a seal 132 in the opening 428 which prevents the seepage of waste out of the pressure vessel 420. The shaft 424 is supported at one end by a bearing 134, located outside of the pressure vessel 420. The shaft 120 of the agitating mechanism 68, which connects to an eccentric rotating arm 430 in the pressure vessel 420, is connected to the driver 70, the electric motor 122 in preferred embodiment via a gear drive 124.

Figure 18:
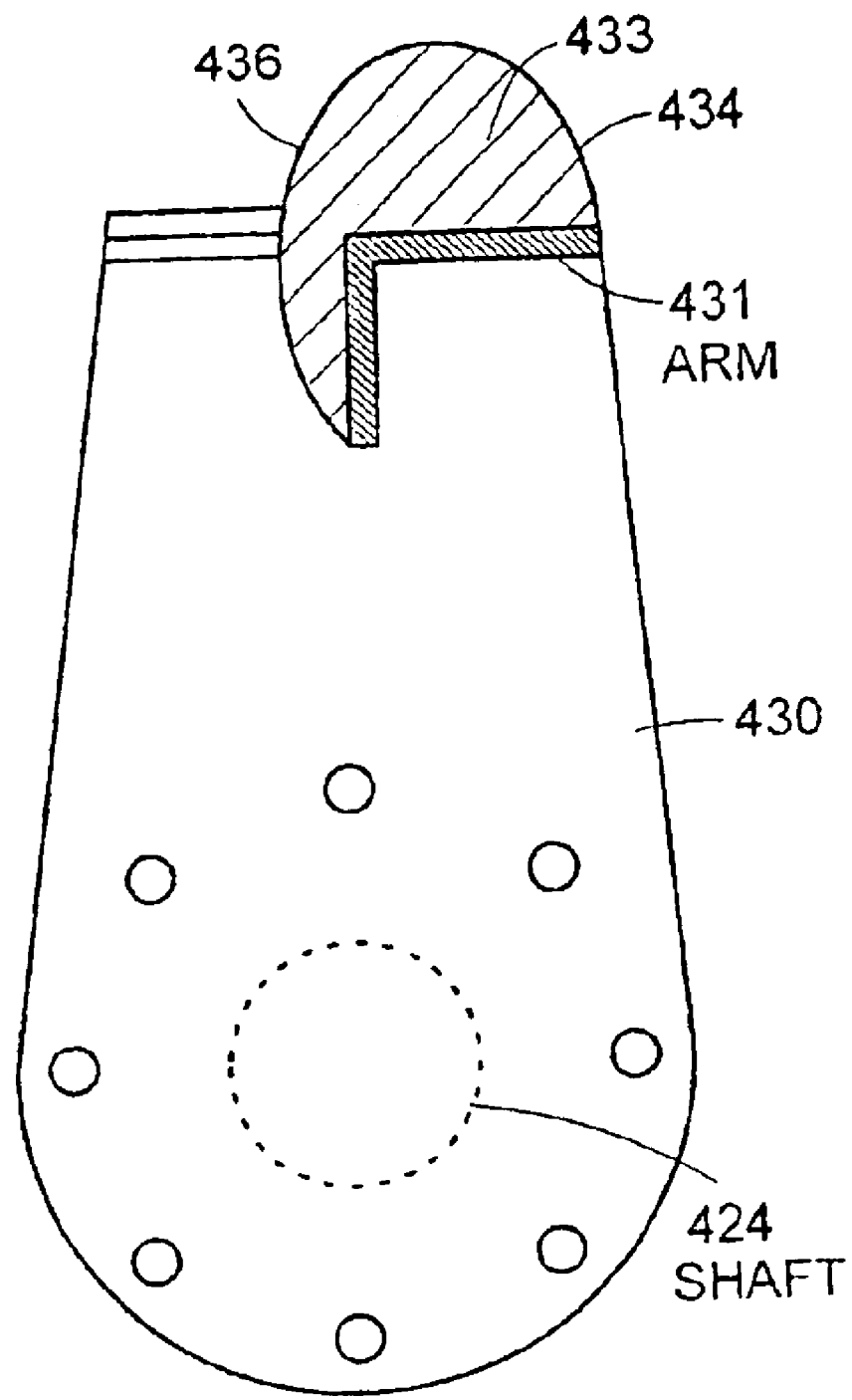
FIG. 18 is a front view of an eccentric rotor with horizontal arm and blades.

Referring to FIGS. 17 and 18, the agitating mechanism 426 includes the shaft 120, the eccentric rotating arm 430, a horizontal arm 431, and a plurality of paddles 433 each having a blade 434. The eccentric rotating arm 430 extends from the shaft 424 towards the wall 82 and receives the horizontal arm 431

The paddle 433 of the agitating mechanism 68, which each have a blade 434, are connected to the horizontal arm 431. The blades 434 are generally cylindrical in shape and are angle such that one side generally moves the waste in a series of planes perpendicular to the eccentric rotating arm 430 as the shaft 120 rotates in one direction. The other side of the blade are faced such that the waste is moved towards the end of the pressure vessel 420 that has the single port 422 when the shaft 120 is rotated in the opposite direction.

The pressure vessel 420 also has a hole 432, as seen in FIG. 17, to which the venting/filter system 100 is connected. The pressure vessel 420 in addition has a minimum of other smaller openings for monitors or sensors, such as a pressure sensor and a temperature sensor.

Still referring to FIG. 17, similar to the embodiments discussed above, a heating jacket 64 in a preferred embodiment is a steam jacket and is defined by the wall 82 of the pressure vessel 420 and the outer exterior wall 86. In addition to opening to allow access to openings in the wall 82 of the pressure vessel 420, the outer exterior wall 86 has additional openings for allowing steam from the steam line into the space 84 in the steam jacket 64, an opening to the steam trap for the collection of condensed steam; and an opening for the removal of trapped air in the steam jacket 64.

The pressure vessel 420 has a knife edge 436 on the edge the blades 434. The knife edge 436 interacts with a series of blocks 438 carried on the walls 82 of the pressure vessel 420, and on the upper half of the pressure vessel 420 in one embodiment. The blocks 438 hinder rotation of the waste to allow the blades to cut the waste.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for sterilizing waste comprising the steps of:
providing a pressure vessel encased by a heating jacket and an electronic control system, the vessel having a plurality of paddles carried by a shaft, the paddles disposed along the length of the pressure vessel;
loading waste into the pressure vessel;
sealing the pressure vessel to allow pressurization of the pressure vessel;
providing heat to the heat jacket to heat the walls of the pressure vessel thereby increasing the temperature and pressure inside the pressure vessel;
rotating the paddles at a rate of 50 revolutions per minute (RPM) or less such that the waste contacts the heated walls of the pressure vessel;
cutting waste entangled or caught on the paddle with a blade;
maintaining the increased temperature and pressure inside the pressure vessel while continuing to rotate the shaft, such that the waste is subjected to a temperature and pressure sufficient to sterilize the waste;
following sterilization of the waste, reducing the pressure in the pressure vessel to remove moisture from the sterilized waste; and
monitoring the pressure vessel during the process with the control system to control the process.

2. The process as in claim 1 wherein the monitoring includes the monitoring of pressure and temperature in the pressure vessel and the controlling of the heat jacket.

3. The process as in claim 2 wherein the temperature is at least monitored at the lowest portion of the pressure vessel.

4. The process as in claim 2 wherein the step of reducing the pressure comprises venting the gas through a vent having a filter for limiting the flow of particulates and further comprising the step of monitoring the flow rate of the gas from the pressure vessel and creating a backflow through the vent to clear the filter.

5. The process as in claim 4 further comprising the step of cooling the gas vented from the pressure vessel prior to discharging the gas.

6. The process as in claim 1 wherein the paddles have blades with knife edges and further comprising a plurality of protrusions carried on the wall of the pressure vessel wherein the protrusion interact than the knife edges of the blade for the step of cutting of waste entangled or caught on the blades.

7. A process for breaking down waste comprising the steps of:
providing a pressure vessel encased by a heating jacket and a plurality of paddles extending from a shaft towards the walls of the pressure vessel;
loading waste into the pressure vessel;
sealing the pressure vessel to allow pressurization of the pressure vessel;
providing heat to the heat jacket to heat the walls of the pressure vessel thereby increasing the temperature and pressure inside the pressure vessel;
rotating the shaft at a rate of 50 revolutions per minute (RPM) or less so that the paddles mechanically causes the waste to contact the heated walls of the pressure vessel; and
cutting waste with a cutting edge in the pressure vessel.

8. The process as in claim 7 wherein the paddles have blades that include knife edges.

9. The process as in claim 8 wherein the knife edges interact with protrusions carried by the wall of the pressure vessel in an upper region of the pressure vessel.

10. A process as in claim 8 wherein:
following sterilization of the waste, venting the gas of the pressure vessel through a vent, having a filter that limits the flow of particles out of the pressure vessel, to reduce the pressure in the pressure vessel to atmospheric pressure, while continuing to heat the pressure vessel and while continuing to rotate the shaft, so as to remove substantially all of the moisture form the sterilized waste, the filter limits the flow of particulates out of the pressure vessel.

11. The process as in claim 10, further comprising the steps
monitoring the flow rate of the gas from the pressure vessel and creating a backflow through the vent to clear the filter when determine that the filter is clogged; and
cooling the gas vented from the pressure vessel prior to discharging the gas.

12. The process as in claim 7 wherein the cutting edges are carried by the wall of the pressure vessel.

13. An apparatus for the treatment of waste comprising:
a substantially horizontally disposed cylindrical pressure vessel;
a heating jacket surrounding substantially all of the pressure vessel for heating the walls of the pressure vessel;
a shaft projecting into the pressure vessel driven by a drive mechanism;
a plurality of paddles carried by the shaft, the paddles being adapted to urge waste in the pressure vessel towards and into contact with the heated walls of the pressure vessel to effect substantially uniform heating thereof;
a plurality of knife edges and protrusions for working in cooperation for cutting of waste entangled on paddles;
at least one port for accessing the pressure vessel for the waste, the port capable of being sealed;
a vent connected to the pressure vessel for reducing the pressure in the pressure vessel to atmospheric pressure; and
a monitor for monitoring parameters of the apparatus and controlling input to the apparatus for at least a portion of the apparatus so that sterilization is achieved.

14. The apparatus of claim 13 wherein the parameters include temperature in the pressure vessel and pressure in the pressure vessel.

15. The apparatus of claim 14 wherein the temperature is monitored by a temperature sensor located in the lower region of the pressure vessel.

16. The apparatus of claim 13 wherein the vent has a narrow area and enlarged area for reducing the velocity of the gas and has a filter for limiting the flow of particulates.

17. The apparatus of claim 13 further comprising a vented emission treatment system having a vapor condensing system with a cooling system for condensating at least a portion of the gas into a liquid and the vented emission treatment system having a vapor portion for filter gas.

18. The apparatus of claim 13 wherein the paddles each have at least one blade having a knife edge in proximity to the wall of the pressure vessel and wherein the protrusions are carried by the wall of the pressure vessel.

19. The apparatus of claim 18 wherein the protrusions are carried by the wall of the pressure vessel on the upper region of the pressure vessel.

20. The apparatus of claim 13 wherein the knife edges are carried by the wall of the pressure vessel.

21. An apparatus for the treatment of waste comprising:
a substantially horizontally disposed cylindrical pressure vessel;
a shaft projecting into the pressure vessel driven by a drive mechanism at a rate of approximately 50 revolutions per minute (RPM) or less;
a plurality of paddles for mixing attached along the length of the shaft, the paddles being adapted to urge waste in the pressure vessel towards and into contact with the heated walls of the pressure vessel to effect substantially uniform heating thereof;
at least one port for the waste capable of being sealed; and
a plurality of knife edges and protrusions for working in cooperation for cutting of waste entangled on the paddles.

22. The apparatus of claim 21 further comprising:
a steam jacket surrounding substantially all of the pressure vessel for heating the walls of the pressure vessel
a vent connected to the pressure vessel for reducing the pressure in the pressure vessel to atmospheric pressure; and
a monitor for monitoring parameters of the apparatus and controlling the thermal inputs and the rotating shaft.

23. The apparatus of claim 21 wherein the paddles each have at least one blade having the knife edge and in proximity to the wall of the pressure vessel and the protrusion are carried by the wall of the pressure vessel on the upper region of the pressure vessel.

* * * * *